United States Patent
Nelson et al.

(10) Patent No.: US 7,019,642 B2
(45) Date of Patent: Mar. 28, 2006

(54) WIDE AREA MULTIPURPOSE TRACKING SYSTEM

(75) Inventors: Bernard C. Nelson, Bloomington, MN (US); Carlos M. Lugtu, Minneapolis, MN (US)

(73) Assignee: Medical Tracking Systems, Inc., Minneapolis, MN (US)

( * ) Notice: Subject to any disclaimer, the term of this patent is extended or adjusted under 35 U.S.C. 154(b) by 4 days.

(21) Appl. No.: 10/648,036

(22) Filed: Aug. 26, 2003

(65) Prior Publication Data

US 2005/0248452 A1 Nov. 10, 2005

Related U.S. Application Data

(63) Continuation of application No. 09/971,260, filed on Oct. 4, 2001, now Pat. No. 6,653,937, which is a continuation of application No. 08/540,943, filed on Oct. 11, 1995, now Pat. No. 6,333,690, which is a continuation of application No. 08/412,646, filed on Mar. 29, 1995, now abandoned.

(51) Int. Cl.
*G08B 1/08* (2006.01)
*H04B 1/06* (2006.01)

(52) U.S. Cl. .............. 340/539.1; 340/539.13; 340/825.36; 340/825.49; 340/572.1; 455/249.1; 455/234.1; 455/250.1

(58) Field of Classification Search ............. 340/539.1, 340/539.13, 572.1, 825.36; 455/33.4, 9, 455/10, 49.1, 234.1, 250.1, 52.1, 52.3, 133, 455/136, 249.1; 342/357.01–357.04
See application file for complete search history.

(56) References Cited

U.S. PATENT DOCUMENTS

| | | | |
|---|---|---|---|
| 4,553,105 A | 11/1985 | Sasaki | 330/145 |
| 4,619,002 A | 10/1986 | Thro | 455/226 |
| 5,184,349 A | 2/1993 | Riordan | 370/95.3 |
| 5,287,414 A | 2/1994 | Foster | 382/1 |
| 5,321,849 A | 6/1994 | Lemson | 455/67.1 |
| 5,363,425 A | 11/1994 | Mufti et al. | 379/38 |
| 6,333,690 B1* | 12/2001 | Nelson et al. | 340/539.21 |
| 6,653,937 B1* | 11/2003 | Nelson et al. | 340/539.1 |

OTHER PUBLICATIONS

"Confidential Private Placement Memorandum", *Medical Tracking Systems*, (Sep. 1994).
"Wescom ILS-3000TM Intelligent Locator System", *Company Brochure, Westcom, Inc.*, (1994).

(Continued)

*Primary Examiner*—Donnie L. Crosland
(74) *Attorney, Agent, or Firm*—Schwegman, Lundberg, Woessner and Kluth P.A.

(57) ABSTRACT

A method of electronically tracking and locating a very large number of objects such as, but not limited to, personal case files in health care, law, or human services systems is described. Each object to be tracked has an attached miniature radio transmitter called a tag which sends a coded signal to a network of receiver base stations with limited but overlapping reception ranges. Each receiver base station places in its own memory the time at which a record enters its range, remains in range, and the time at which it leaves. The various receiver base stations are interconnected to a host computer. By polling the memories of each receiver base station, the computer is able to determine the current location of any record.

27 Claims, 20 Drawing Sheets

OTHER PUBLICATIONS

Fletty, S., et al., "A Multipurpose RF Tracking System. EE5450 Senior Design Final Report", *Presented at Univ. of Minnesota*, (Aug. 24, 1994).

Morrissey, J., "Information gets to the Point Without Wire", *Modern Healthcare Weekly Business News*, (Mar. 1994),94-96.

Pountain, D., "Track People with Active Badges", *Byte*, (Dec. 1993),57-64.

* cited by examiner

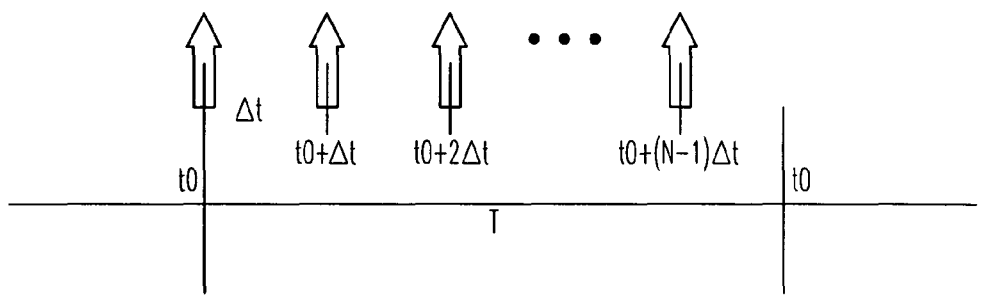
Fig.17
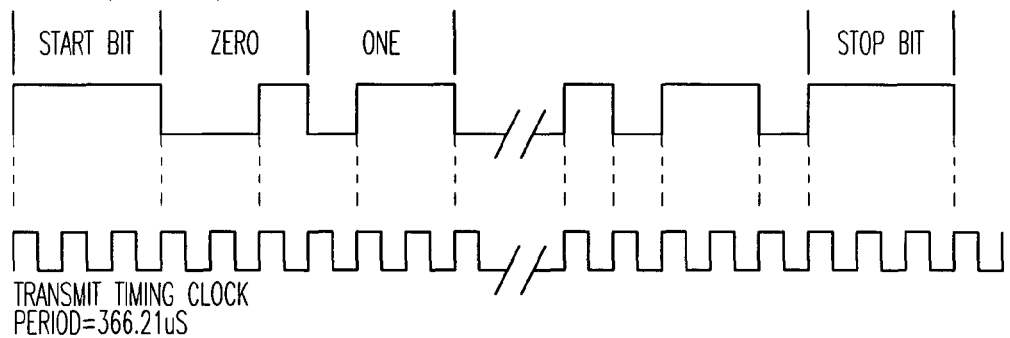
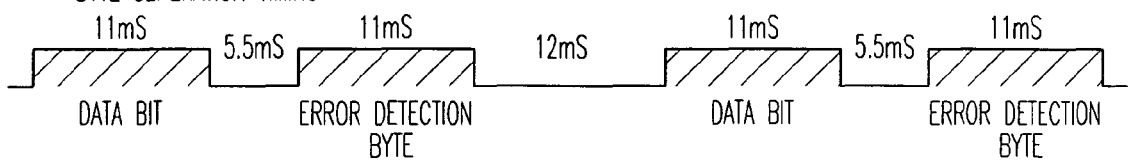
Fig.18

WIDE AREA MULTIPURPOSE TRACKING SYSTEM

This is a continuation of application Ser. No. 09/721,260, filed Oct. 4, 2001, now U.S. Pat. No. 6,653,937, which is a continuation of application Ser. No. 08/540,943, filed Oct. 11, 1995, now U.S. Pat. No. 6,333,690, which is a continuation of application Ser. No. 08/412,646, filed Mar. 29, 1995, now abandoned.

FIELD OF THE INVENTION

The present invention relates to remote tracking of objects and in particular to remote tracking and accounting of records, equipment, and any movable object.

BACKGROUND OF THE INVENTION

Present day businesses expend great amounts of financial and personal resources in attempting to locate and manage objects, including records, equipment, and people. However, present day recordkeeping systems are ineffective at locating these objects.

Many objects must be located quickly to save loss of life and property. For instance, in the hospital setting, patients who are critically ill can best be treated when their physician has their complete medical record in hand. Oftentimes, their records are not available to the treating physician because they have been lost or misplaced. The cost and time dedicated to finding them becomes expensive and potentially life-threatening.

When conditions are not life-threatening, losses are incurred by the health system as a whole, since extra tests are given, delays in diagnosis occur, and major delays in billing result because, for periods of time, these records are lost and cannot be found.

One attempt at tracking file folders, for example, is given in U.S. Pat. No. 5,287,414 whereby an optical scanner mounted to the file drawer is used to detect files stored in the filing cabinet so that, upon opening or closing the filing cabinet drawer, all the files in that drawer are scanned. The scanned folders are logged as being located in that drawer by a computer system. A major drawback of this system is its inability to account for files unless they are located within a filing cabinet drawer.

Attempts at tracking materials and people have also been made, for example, in U.S. Pat. No. 5,363,425, whereby an identification badge containing a radio frequency transmitter is located across a telephone network by receiver units in or near telephone sets. However, this invention teaches the use S of random transmissions from the identification badges, which is not applicable to systems containing a number of transmitters because of overlapping or "colliding" of transmission bursts.

An attempt at tracking persons was made by an infrared active badge as described in the December 1993 Byte article "Track People With Active Badges". This reference teaches the use of infrared transmitters because of their ready availability in television and video recorders and because the signals bounce off of walls which compensates for their directivity. However, the infrared technology disclosed is inadequate for applications where the transmitter is covered by a surface which blocks transmission of infrared light. This design also requires more receivers per installation due to the opacity of objects to infrared light.

Therefore, there is a need in the art for an inexpensive tracking system for a collection of objects which is capable of tracking a large number of objects. Such a tracking system must be able to track objects within an entire room or group of rooms and detect objects even if there is no clear optical path between the beacons and the detecting system. There is also a need for a low power, low cost beacon design to control the overall cost of the tracking system. Additionally, there is a need for a system having a minimal number of receivers to control the cost of the system and the invasiveness of the installation, and the receivers should have an effective means for transferring information to a central processor for processing location information.

SUMMARY OF THE INVENTION

The present invention solves the aforementioned problems and shortcomings of the existing art and solves other problems not listed above which will become apparent to those skilled in the art upon reading and understanding the present specification and claims.

The present invention is a multipurpose tracking system which is capable of tracking any movable object. For purposes of illustration, this discussion will center on one embodiment of the present invention which relates to the tracking of medical records using a plurality of transmitting tags ("tag"s) and one or more receiver base stations ("RBS"s). This embodiment reduces the problems associated with tracking of objects such as files, equipment or people by electrically tracking the records as they are moved about the hospital. Tracking is performed by transmitting tag specific identification and error correction information by each tag to one or more RBSs. Tag information is time stamped and transferred by the RBSs to a central processor which uses the tag information to locate a tag (and its attached file). Tags are located by associating a RBS site for each file in the system. An individual record locator or "sniffer" is also taught which may be used to locate a record located in a large cell range.

In this embodiment the tags are assigned their own identification code as they are commissioned. Each tag transmits according to a specialized, error-compensated time-multiplex arrangement, which avoids overlap of transmissions, even for large numbers of transmitting tags. Tag timing inconsistencies are corrected by comparing each tag clock with an accurate system clock and the errors are compensated by an offset downloaded to the tag to correct for mistiming. A low power transmitter on each tag provides a long lifetime of each transmitter.

The geometries of the RBS reception ranges are critical, since these geometries determine the scope of each RBS site and the overlap of the sites is beneficial in detecting transition of the record from one RBS site to the next. If the reception ranges overlap, then the transition is continually recorded and the record location is never uncertain. Tailoring the RBS reception range geometries provides accurate tag location detection, even for varying room or hall geometries.

One embodiment of the present invention incorporates a tag programmer for programming the transmitting tags in the tracking system. Details of the tag programmer are also provided below.

Therefore, this embodiment of the present invention solves the deficiencies of the prior art enumerated above and other deficiencies by providing a multipurpose radio frequency tracking system. As mentioned above, other embodiments of the present invention are possible and limited variations will be discussed throughout the specification.

BRIEF DESCRIPTION OF THE DRAWINGS

In the drawing, where like numerals describe like components throughout the several views:

FIG. 17 is a time line showing the timing of transmissions of tag identifiers according to one embodiment of the present invention;

FIG. 18 is a timing diagram of the tag transmission protocol according to one embodiment of the present invention;

DETAILED DESCRIPTION

In the following detailed description, references made to the accompanying drawings which form a part hereof and in which is shown by way of illustration specific embodiments in which the invention may be practiced. These embodiments are described in sufficient detail to enable those skilled in the art to practice and use the invention, and it is to be understood that other embodiments may be utilized in that electrical, logical, and structural changes may be made without departing from the spirit and scope of the present invention. The following description is, therefore, not to be taken in a limiting sense and the scope of the present invention is defined by the appended claims and equivalents thereof.

Figure 1:
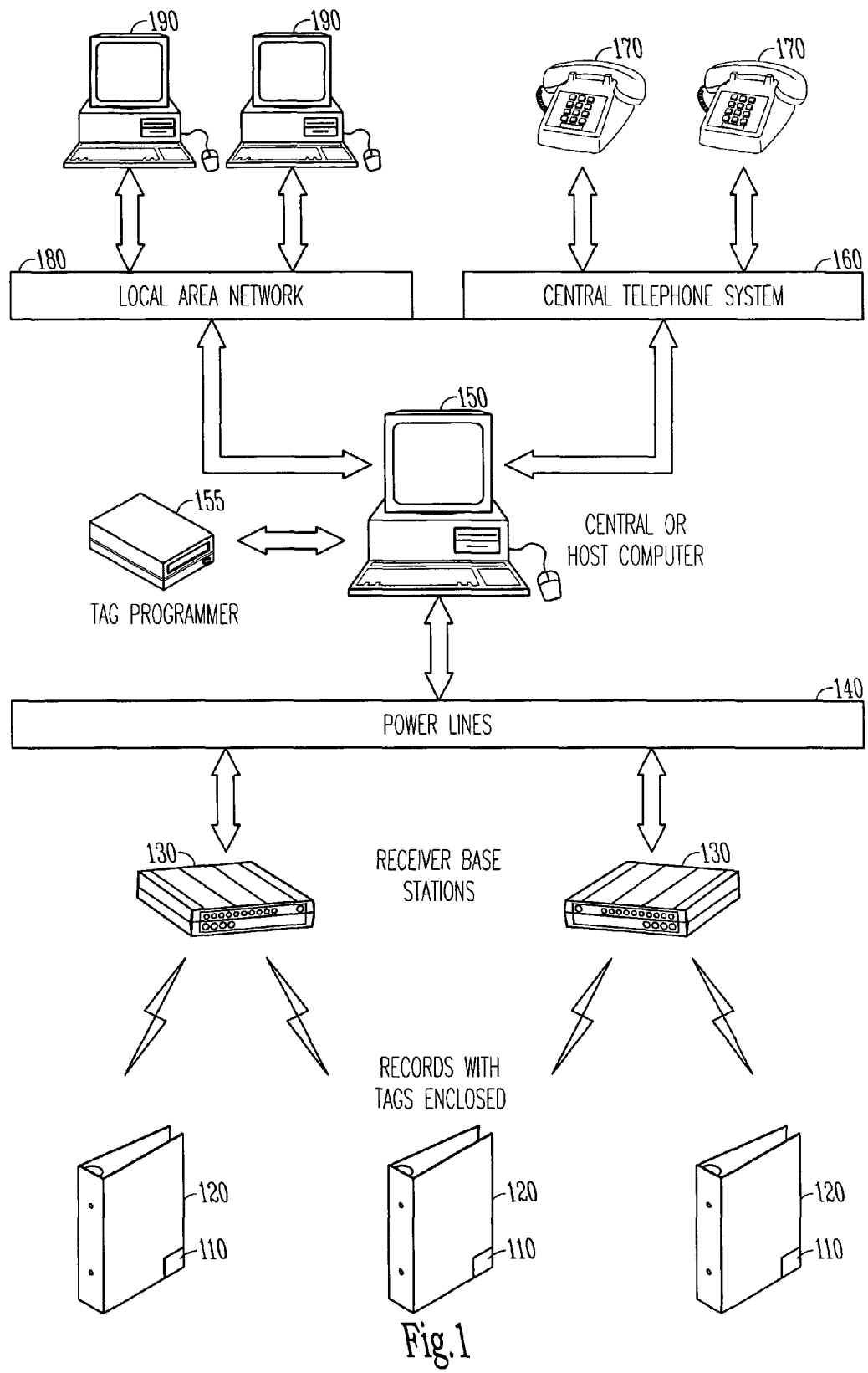
FIG. 1 shows a record tracking system according to one embodiment of the present invention.

FIG. 1 shows a record tracking system according to one embodiment of the present invention. In this embodiment, tags 110 are programmed by tag programmer 155 in conjunction with host computer 150 before being attached to a record 120. Tags 110 are each programmed with an identification number and timing information during their initial programming. A program on host computer 150 coordinates the issuance of tag identification numbers and associates them with the record 120 to which the tag 110 is attached. The tag 110 may be programmed with other information, including the identity of the record 120 associated with the tag 110 and other time and date information.

In this embodiment, receiver base stations (RBS) 130 receive transmissions emanating from tags 110 as they approach the reception range around each individual RBS 130. Tag identification information is transferred by RBSs 130 to the host computer 150 via modulations over the ac power lines 140 which interconnect RBSs 130 and host computer 150. One skilled in the art would recognize that other communications means may be employed without departing from the spirit and scope of the present invention. For example, the communications between RBSs 130 and host computer 150 may be over radio frequency link, cellular phone link, telephone line link, dedicated hardwired link, computer network link, or any combination of these links.

The local area network 180 and terminals 190 are not essential parts of this embodiment of the present invention, however, serve to illustrate how the information collected from the tracking system could be disseminated to other destinations. Likewise, although the telephones 170 and telephone lines 160 are not essential parts of the present invention, they illustrate that the data acquired by the tracking system could be accessed via telephone. For example, a variation of the present invention would allow an office worker to call the host computer 150 and inquire about the location of a particular record based on inputs from tags 110 and processing as performed on host computer 150.

In a record tracking scenario, tags 110 are attached to records 120 at the time they are checked out of the records department. Each tag 110 is assigned a unique identification code which is associated with the record 120 to which the tag 110 is attached. The host computer 150 will be used to manage the association of ID codes to tags 110, and tags 110 to records 120. This association will later be used by the host computer 150 to track and locate the records 120. Records personnel will be responsible for attaching the tags 110 to the records 120 as they check them out of the records department. When a record 120 is to be checked out, the record number will be entered into the host computer 150, which then instructs the records personnel to place a tag 110 into the tag programmer 155. Once this connection has been made, the host computer 150 will download the identification code, the current time, and other relevant information to the tag 110. Once the tag 110 is programmed it is attached to the record 120 and is free to leave the records area. The tag programmer 155 is used again when the record 130 is returned to the archives. The tag 110 is removed from the record 120 and again placed in the tag programmer 155, its identification code is read and is available for use with another record 130. Finally, the tag's 110 transmitter is turned off to conserve battery life.

Figure 2:
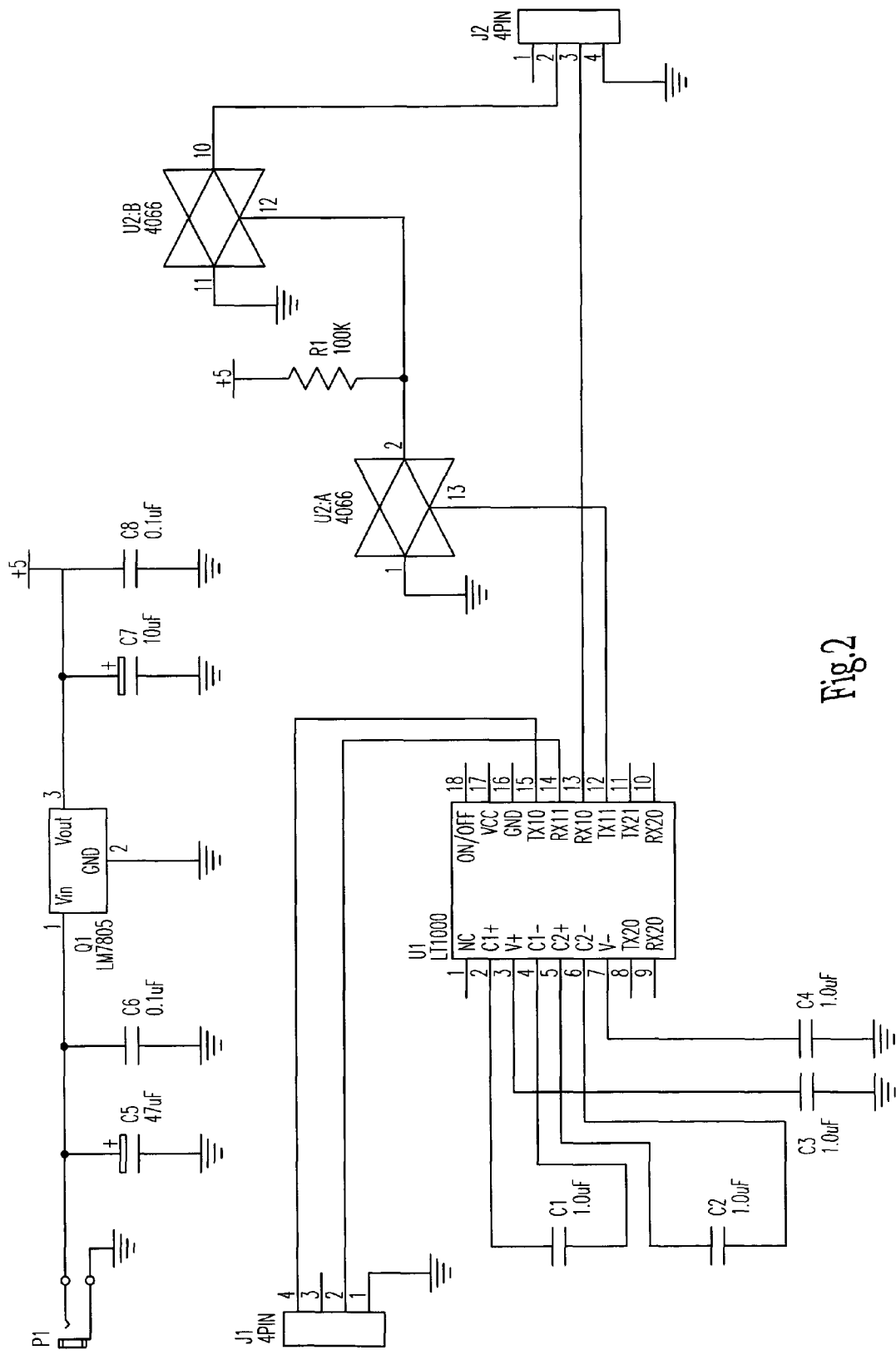
FIG. 2 is a schematic diagram of one embodiment of a tag programmer for programming transmitting tags according to one embodiment of the present invention.

A schematic diagram of one embodiment of a tag programmer 155 is shown in FIG. 2. The cost and complexity of each tag 110 is reduced since the interface for programming the tag 110 is less expensive than incorporating on-tag electronics for programming the tag 110. U1 is a Linear Technologies LT1080, which is an RS232 interface driver used to provide level shifting between RS232 and 0–5 volt levels (at the programmer). U2 is used to provide additional level shifting of 0–5 volt levels down to 0–3 volt levels to make the tag programmer 155 compatible with the voltage levels used on the tag 110. J1 provides for the connection to the host computer 150. J1, pin one is common ground between the tag programmer 155 and the host computer 150. J1, pin two is for data received into the tag programmer 155 from the host computer 150. J1, pin 4 is for data sent from the tag programmer 155 to the host computer 150. J2 provides for connection to the tag 110. J2, pin two is for data sent from the tag programmer 155 to the tag 110. J2, pin 3 is for data received into the tag programmer 155 from the tag 110. J2, pin 4 provides a common ground between the tag 110 and the tag programmer 155. The tag programmer 155 is used to initialize the tag 110 when it is to be placed in a record 120 and again to decommission the tag 110 when the record 120 is returned.

To accommodate tracking of the tags 110 and the associated records 120, receiver base stations (RBS's) 130 will be placed at strategic locations throughout the institution. When a tag 110 transmits within the reception range of a particular RBS 130, the RBS 130 will read the identification number of that tag 110 and store the ID number along with the time of reception into memory. The RBS's 130 will continually record the activity of tags 110 within their range and store this information to memory. Periodically, the contents of the RBS memory will be downloaded to the host computer 150. The host computer 150 will sort and manipulate this data so that record personnel can locate records 120. The host computer 150 will also provide a telephone interface so that any personnel in the institution may call the host computer 150 and access record location information by entering commands over a touch-tone telephone 170.

Figure 3:
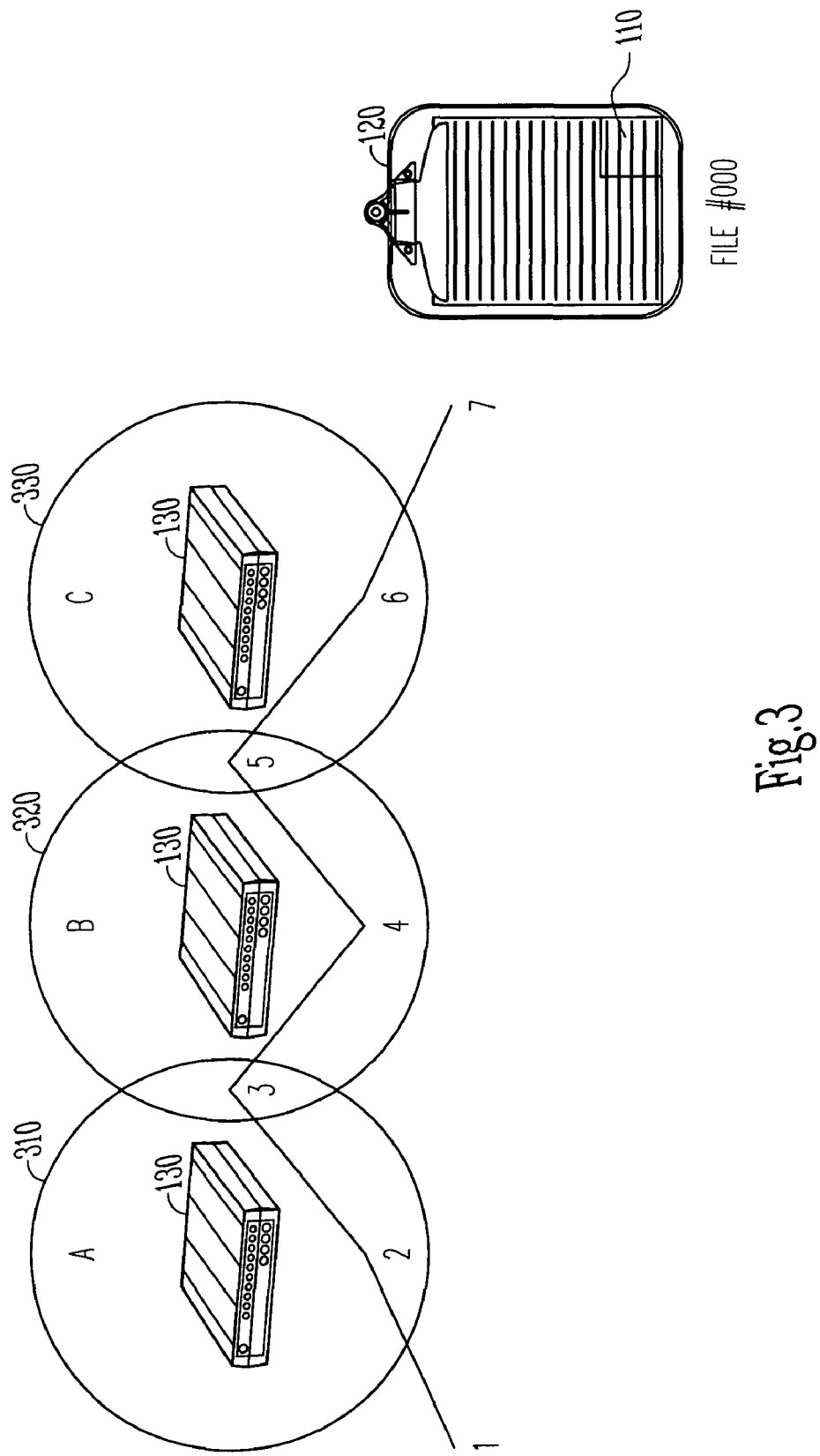
FIG. 3 shows overlapping receiver base station reception ranges and a hypothetical path of a single record as one example of record tracking according to one embodiment of the present invention.

FIG. 3. shows one example of the location tracking scheme using three RBSs 130 as a tag 110 passes through their respective reception ranges. The reception ranges 310, 320 and 330, respectively of RBSs A, B, and C are shown as omnidirectional (isotropic) reception ranges, however, those skilled in the art will recognize that other nonisotropic reception ranges are possible using different receiving antenna configurations, and that the use of such nonisotropic reception ranges will not depart from the scope and spirit of the present invention. The RBSs A, B, and C will record periodic transmissions from the roving tag 110 and log each transmission according to the identification code sent by the tag 110, the time and date. The recordings are combined to form a transmission log which is periodically reported to the host computer 150. Host computer 150 processes the transmission log and presents the resulting record locations to users.

The sensitivity of the RBS receiver section is adjustable to control the size of the reception range for each RBS 130. Reception ranges may vary from between just a few feet to as much as 100 feet. Sensitivity adjustments are accomplished by adding an attenuator in series with the RBS antenna or by modifying the reception pattern of the antennas located on the RBS 130. Adjustments to reception range are helpful in controlling the overlap of adjacent RBSs 130 and in tuning the resolution of reception for a particular application. For example, in a tracking application in a warehouse environment, the reception range may be large (i.e., relatively little resolution needed) for applications which need to determine if a tagged object is in the warehouse. Resolution must be increased if another application requires knowledge of which warehouse aisle the tagged object is located. Adjustability of the RBS reception range provides the necessary resolution, depending on the application.

Table 1, below, shows a hypothetical transmission log for the system of FIG. 3 and the processed data for the record path delineated in FIG. 3.

TABLE 1

| RBS Compiled Transmission Logs | | |
|---|---|---|
| RBS | In | Out |
| A | 1:00 PM | 1:10 PM |
| B | 1:08 PM | 1:18 PM |
| C | 1:16 PM | 1:26 PM |

| Processed Location Data Logs | | | |
|---|---|---|---|
| Record Path | Areas | In | Out |
| 1 | . . . A | — | — |
| 2 | A | 1:00 PM | 1:08 PM |
| 3 | AB | 1:08 PM | 1:10 PM |
| 4 | B | 1:10 PM | 1:16 PM |
| 5 | BC | 1:16 PM | 1:18 PM |
| 6 | C | 1:18 PM | 1:26 PM |
| 7 | C . . . | — | — |

The host computer 150 processes transmission log data to obtain the processed location data. In one embodiment of the present invention, the transmission logs indicate when a transmitter entered or left an RBS's 130 reception range. It is up to the host computer 150 to process the received data to determine record 120 location as a function of time and RBS 130 reception range. For example, since the record 120 was tracked in range A (see FIG. 3) from 1:00 PM to 1:18 PM its best known location is range A. However, the record 120 was received in range B at 1:08 PM. Therefore, the best known location for the record 120 between 1:08 PM and 1:10 PM is the overlapping regions of A and B as shown in the processed location data of Table 1 (third entry). This processing continues for the remaining portion of the transmission log to best determine position of the record as a function of time, given the reception range information. The record can then be located by inspecting the most recently logged transmission. The path of the record through a track can also be evaluated and statistical analysis done. A more detailed description of the record tracking algorithm follows.

One Example of a Tracking Algorithm

Figure 4:
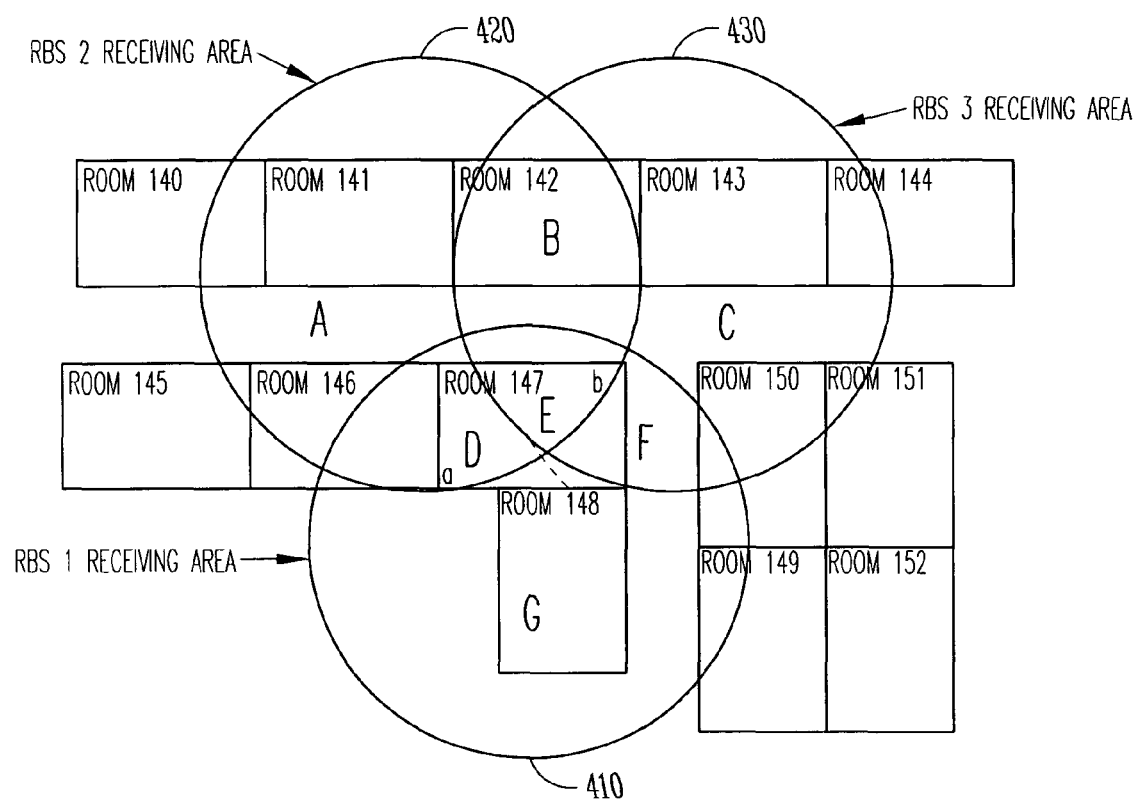
FIG. 4 shows another arrangement of overlapping receiver base station reception ranges and demonstrates the range coverage over a number of rooms in a hypothetical building as one example of record tracking according to another embodiment of the present invention.

FIG. 4 illustrates another reception range arrangement featuring three overlapping reception ranges for finer resolution than that of an individual RBS 130 reception range. Circles 410, 420, and 430 represent the receiving ranges of RBSs 1, 2, and 3 respectively, of FIG. 4. The letters represent tags 110 (or records 120) dispersed in the tracking area. For the sake of illustration, rooms are shown on FIG. 4 and their respective mapping to the reception ranges of the various RBSs 130 of the system. In one embodiment of the present invention the host computer 150 is programmed with the geometric locations of the RBSs and the rooms covered by their reception ranges. Other embodiments feature a special tag with programmable identification codes which may be used to "map" rooms to various RBSs 130, by walking from room to room and changing identification codes on the special tag as each room is entered. As the transmission log is processed by the host computer 150, each room is associated with the identification code used with the special tag transmitter while in the room. Each RBS 130 that detects the special tag within its receiving range will report that information to the host computer 150 and the computer will create a database that associates RBSs 130 to locations. The database on the computer will then contain a list of RBS 130 and their associated rooms. This is illustrated in FIG. 5B. A new tag identification and location is assignable in every uniquely mapped location on FIG. 4 and are labeled as regions A, B, C, D, E, F, and G as shown. Of course, such mappings are functions of the placement of the RBSs, the extent of their reception ranges, and the geometry of their reception ranges (shown are isotropic reception ranges, however, nonisotropic ranges are possible, as stated earlier). Room geometries and absorbing or reflective surfaces may cause deviation of the normal reception pattern, which may be accounted for by the mapping described in this embodiment of the present invention, since the special tag will not be sensed around such radio frequency obstacles.

A list of tags 110 currently within each RBS's 130 reception range may be maintained by the computer system 150. These lists are updated when the RBS 130 reports periodically to the host computer 150 or when queried by the host computer 150. The host computer 150 accounts for tag identification numbers which are actively assigned and those which are retired to ensure that no duplicate tag identification numbers are issued. The host computer 150 also stores the record 120 assignment to each tag 110, which may include other relevant data such as record number, patient name, destined location and other information that an application may require.

Figure 5A:
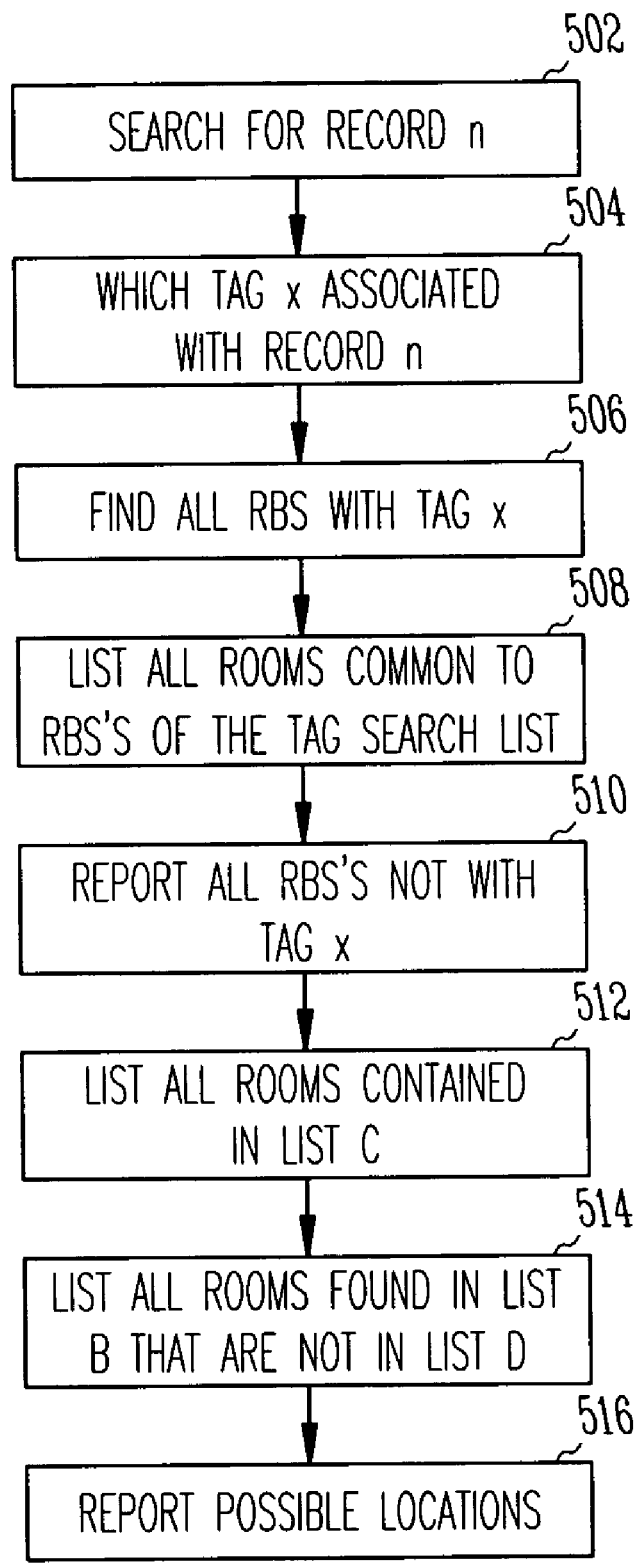
FIG. 5A is a flow diagram showing the general record location algorithm as implemented by the central processor according to one embodiment of the present invention.
Figure 5B:
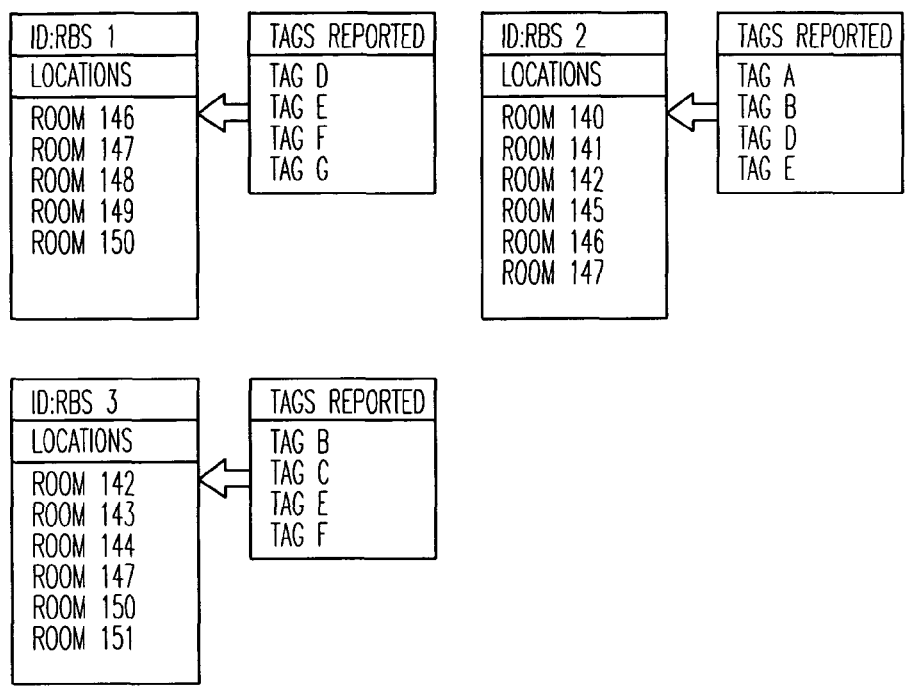
FIG. 5B is a mapping of rooms to receiver base stations and the tags reported according to the reception ranges shown in the hypothetical building of FIG. 4.

The algorithm to locate a record 120 is shown in FIG. 5A. To retrieve a record 120, with identification number n, the host computer 150 finds the related tag identification number x (step 502, 504). The host computer 150 then polls the transmission logs to determine which RBSs 130 are reading the tag 110 with identification number x (step 506), and creates a list A. The host computer 150 then takes the RBSs 130 on list A and maps all of the common rooms associated with each RBS on List A to create List B. The host computer 150 then creates lists C and D in a similar fashion, however, they consist of cells not reporting the desired identification number x (steps 510, and 512). The list of possible locations is determined by the subtraction of Lists B and D per steps 514 and 516 of FIG. 5A.

One skilled in the art will recognize that other variations of the record search procedure may be employed without departing from the scope and spirit of the present invention.

The following four examples are given for illustration and incorporate the hypothetical office structure given in FIG. 4 and FIG. 5B:

EXAMPLE 1 given: record 234123 is associated with Tag E.
Search for record: 234123
Which Tag is associated with record 234123
  Tag E (given)
List all RBSs with Tag E (list A) (see FIG. 5B)
  RBS 1
  RBS 2
  RBS 3
List all rooms that are common to RBS 1, RBS 2, RBS 3 (list B)
  Room 147 [Report Possible locations]
List all RBS not with Tag E (list C)
  <Null List>
List All rooms from previous list (list D)
  <Null List>
List all rooms in list B and not in list D
  Room 147
  [Report identified location]
The record is in room 147

EXAMPLE 2 given: record 235555 is associated with Tag B.
Search for record: 235555
Which Tag is associated with record 235555
  Tag B
List all RBS with Tag B (list A)
  RBS 2
  RBS 3
List all rooms that are common to RBS 2, RBS 3 (list B)
  Room 142
  Room 147
  [Report possible locations]
List all RBS not with Tag B (list C)
  RBS 1
List all Rooms from list C (list D)
  Room 146
  Room 147
  Room 148
  Room 149
  Room 150
List all rooms in list B and not in list D
  Room 142 [Report identified location]
The record is in room 142

EXAMPLE 3 given: record 235335 is associated with Tag D.
Search for record: 235335
Which Tag is associated with record 235335
  Tag D
List all RBS with Tag D (list A)
  RBS 1
  RBS 2
List all rooms that are common to RBS 1, RBS 2 (list B)
  Room 146
  Room 147
  [Report possible locations]
List all RBSs not with Tag D (list C)
  RBS 3
List all Rooms from list C (list D)
  Room 142
  Room 143
  Room 144
  Room 147
  Room 150
  Room 151
List all rooms in list B and not in list D
  Room 146
  [Report identified location]
note: that this identified location is not correct (see FIG. 4)

The record is in room 146

Note that the last example gave a wrong identified location. This can be remedied by dividing certain rooms up into more reception ranges. For example room 147 can be broken up into two reception regions 147*a* and 147*b*.

EXAMPLE 4 given: record 235335 is associated with Tag D.
Search for record: 235335
Which Tag is associated with record 235335
   Tag D
List all RBS with Tag D (list A)
   RBS 1
   RBS 2
List all rooms that are common to RBS 2, RBS 3 (list B)
   Room 146
   Room 147*a*
   Room 147*b*
   [Report possible locations]
List all RBSs not with Tag D (list C)
   RBS 3
List all Rooms from list C (list D)
   Room 142
   Room 143
   Room 144
   Room 147*a*
   Room 147*b*
   Room 150
   Room 151
List all rooms in list B and not in list D
   Room 146
   Room 147*b*
   [Report identified location]
The record is in room 146 or 147*b*

The above examples were simplified for the purpose of illustration. Hallways, and dead spots were not taken into account.

Figure 6:
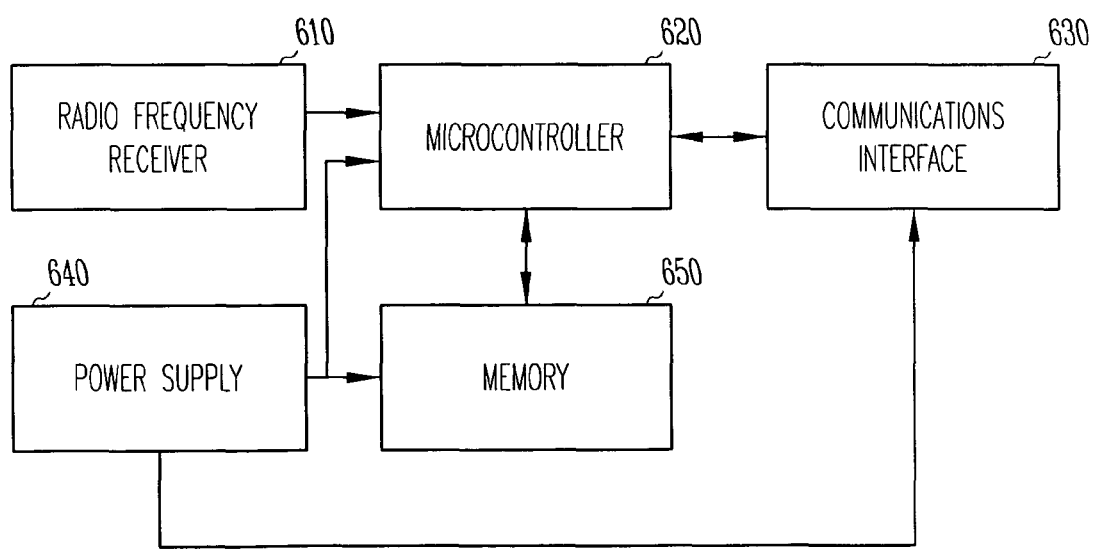
FIG. 6 is a block diagram of a receiver base station according to one embodiment of the present invention.
Figure 7A:
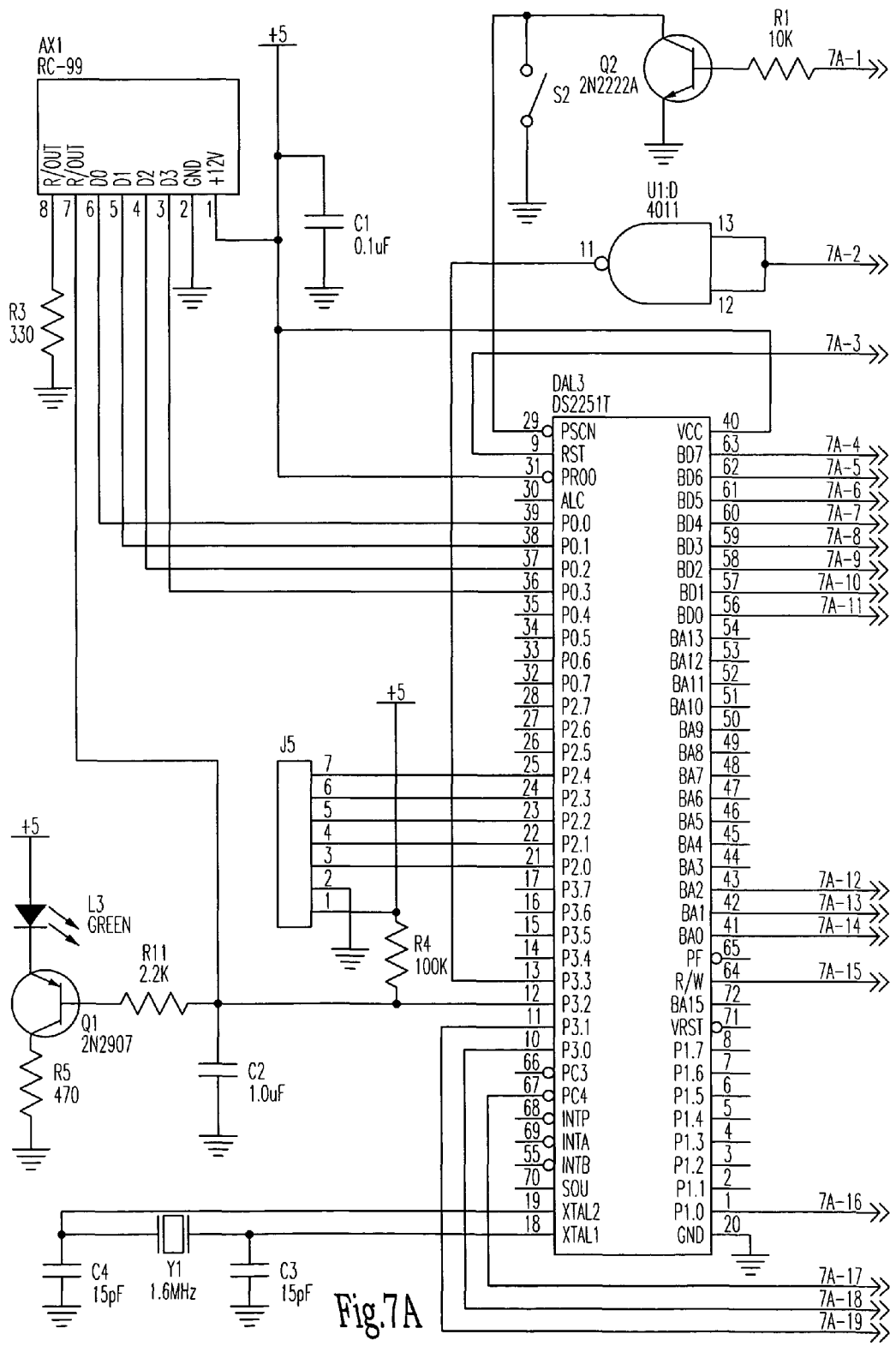
FIG. 7 is a schematic diagram of a receiver base station according to one embodiment of the present invention.
Figure 7B:
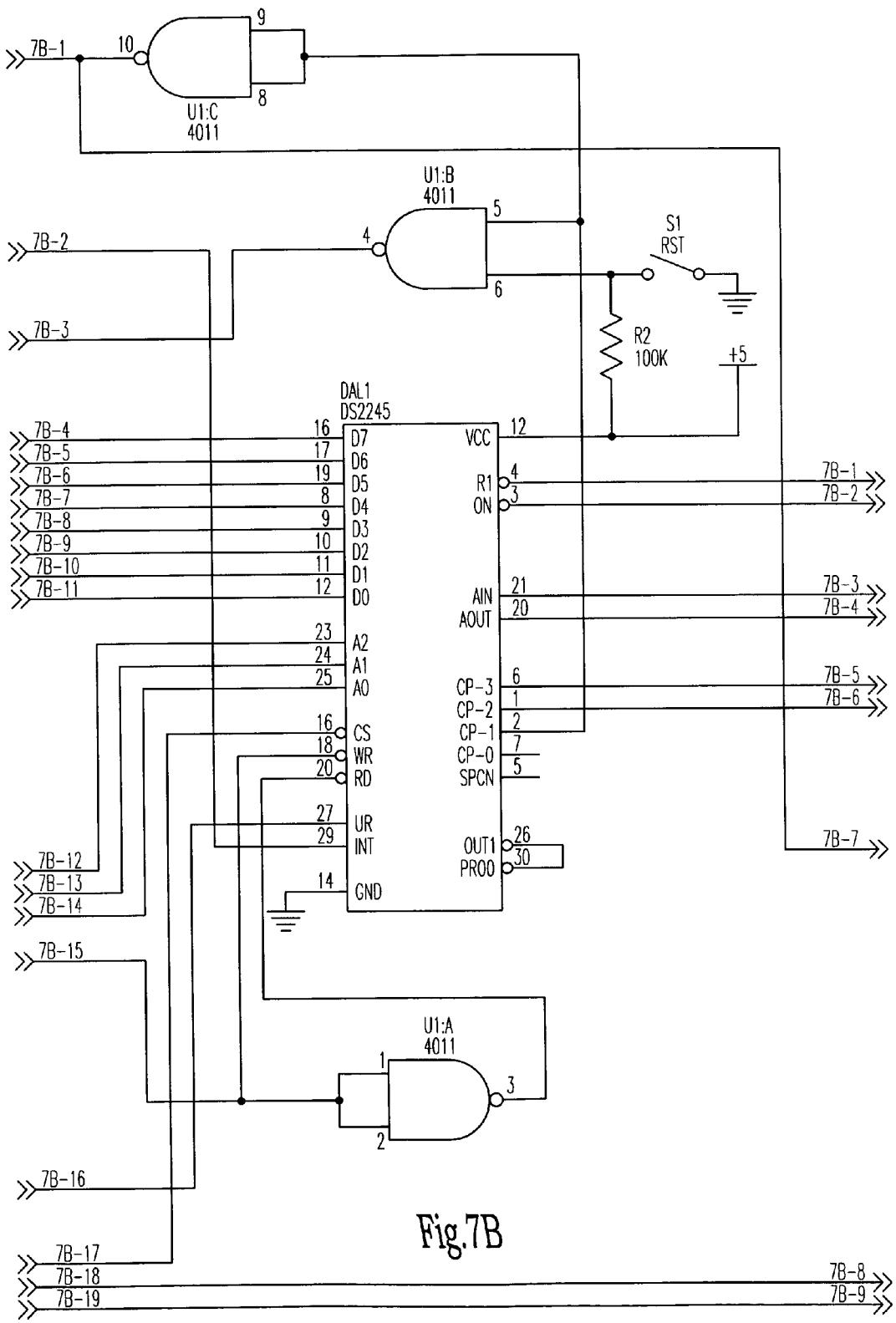
Figure 7C:
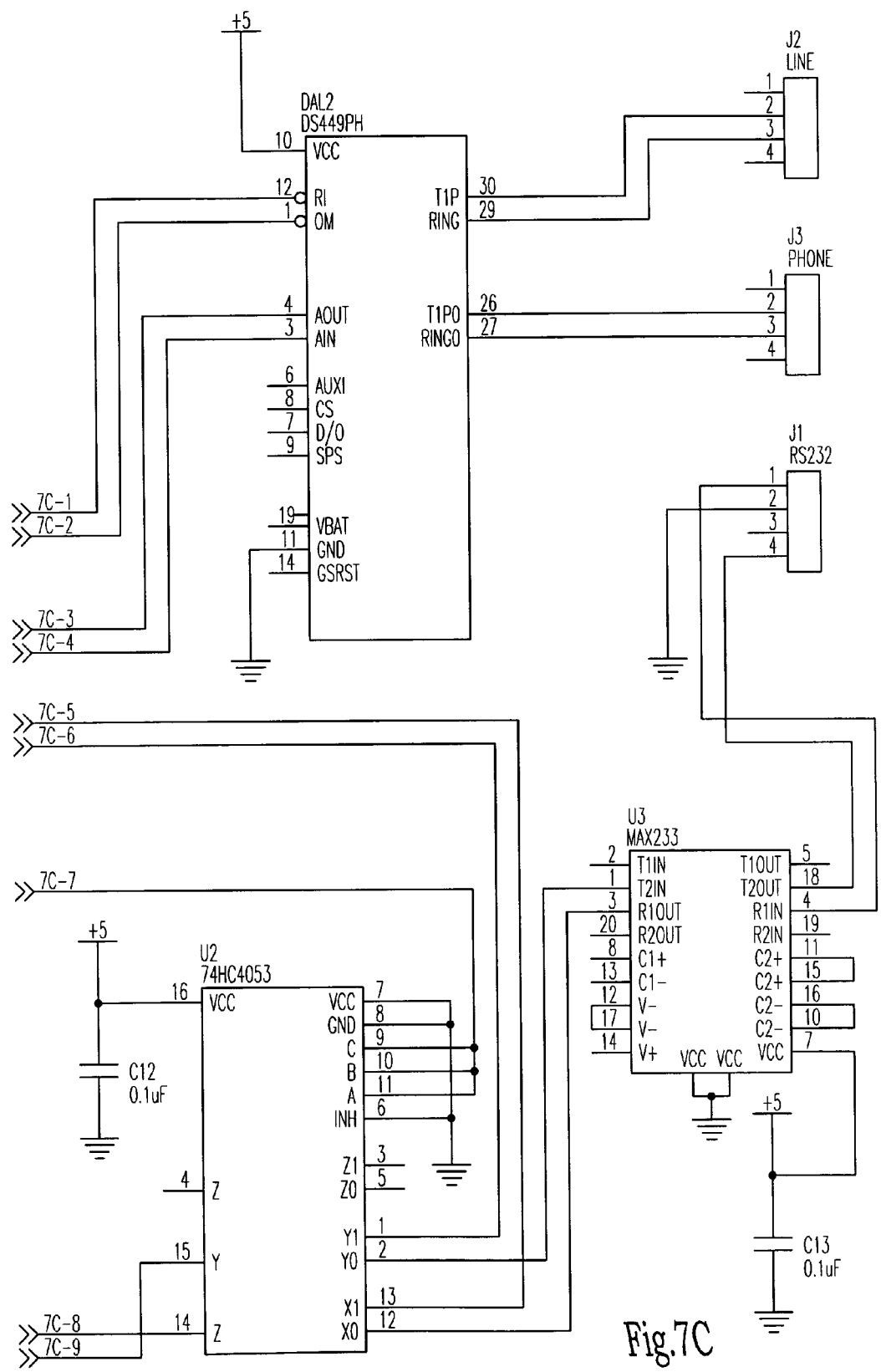
Figure 7D:
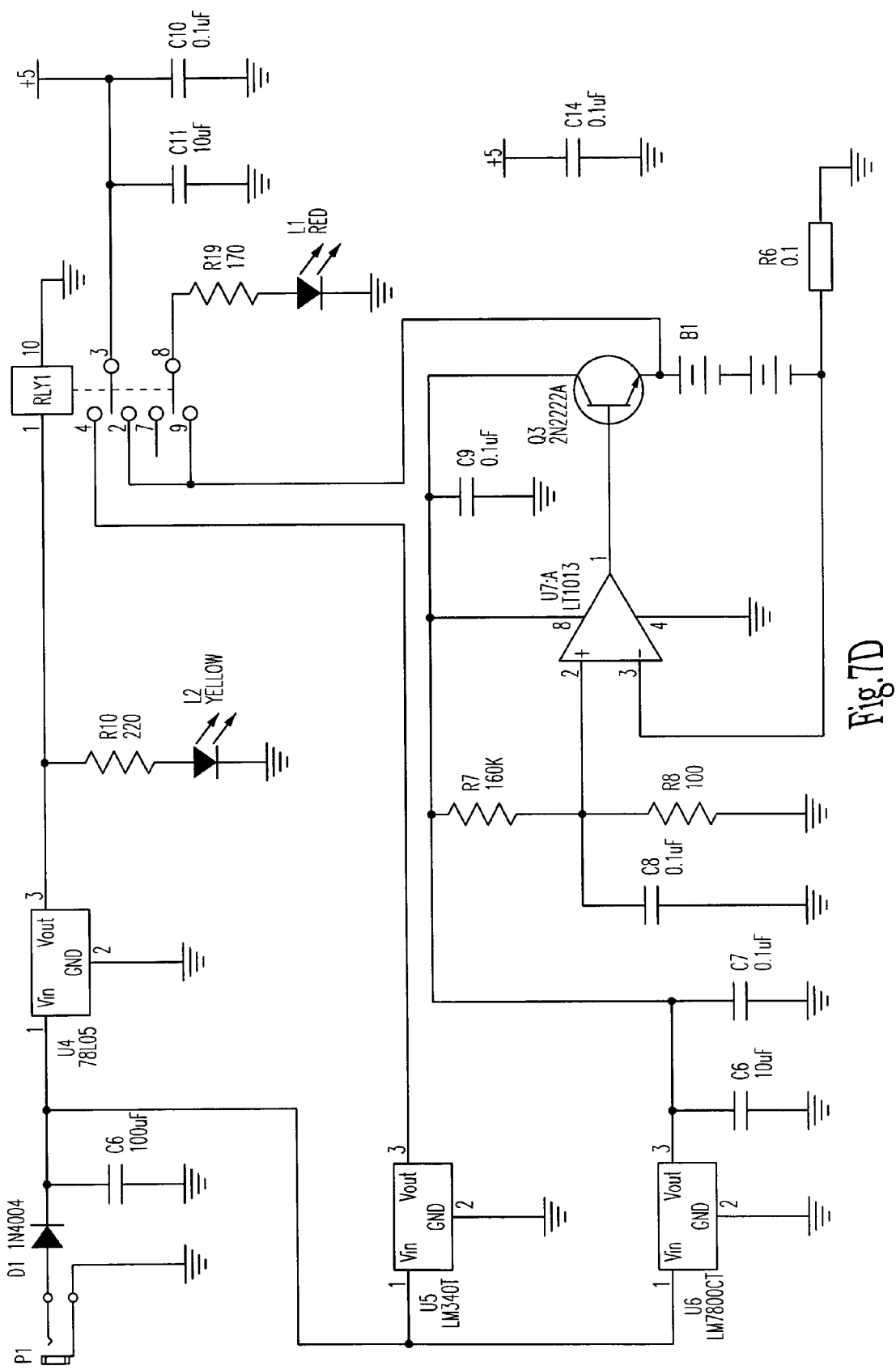

A block diagram of the RBS 130 according to one embodiment of the present invention is shown in FIG. 6 and a schematic diagram according to one embodiment is shown in FIG. 7. FIG. 6 demonstrates the overall structure of the RBS 130, which has an RF receiver 610 connected to a microcontroller 620, which is in turn connected to a communications interface 630. Power Supply 640 powers memory 650 and microcontroller 620. Details of these modules are found in FIG. 7. The receiver module RX1 receives an RF signal from the tags 110 and demodulates a 16 bit identification (ID) code. In one embodiment, RX1 is a receiver module, part no. RE-99, manufactured by Ming Engineering and Products, Inc., and described in further detail by Ming Data Sheet, Doc. No. TR-09 Rev. A1, which is hereby incorporated by reference. RX1 receives signals from tags 110. In this embodiment, RX1 provides four parallel data bits to transfer the received tag ID number to the microcontroller 620. Those skilled in the art will readily recognize that other receivers may be used without departing from the scope and spirit of the present invention.

A sixteen bit ID code provides 65,356 unique ID codes maximum Those with knowledge in the art will readily recognize that more bits could be used if a larger number of ID codes is required. The 16 bit code is transferred to the microcontroller module DAL3 where it is associated with the time and date, then saved in memory. DAL3 is a Data Access Arrangement (DAA), manufactured by Dallas Semiconductor, part no. DS24PH, as described in the Dallas Semiconductor Teleservicing Handbook, 1991, which is hereby incorporated by reference. Microcontroller 620 is embedded in DAL3.

Periodically, the RBS 130 will be called upon to transfer the contents of its memory 650 to the host computer 150. This transfer is accomplished by means of the communications interface 630. The embodiment in FIG. 7 provides both a wired serial communications interface and telephone modem communications interface. The modem is comprised of modules DAL1 and DAL2, connectors J2 and J3, and some miscellaneous components. The serial communications are accomplished with integrated circuit U3 and connector J1. U2 provides for multiplexing between serial and modem communications.

U2 is a multiplexor by National Semiconductor, part number 74HC4053, as described in the National Semiconductor CMOS Databook, 1994, which is hereby incorporated by reference. U2 switches between the serial communication and modem communication modes in the RBS 130.

U3 is an RS232 driver by Maxxim, part no. MAX223, as further described in the Maxxim Data Book which is hereby incorporated by reference. U3 provides voltage level shifting to and from CMOS voltage levels and the RS232 voltage levels.

DAL1 is a microcontroller module manufactured by Dallas Semiconductor, part no. DS2251T6416, and is described further in the Dallas Semiconductor Soft Microcontroller Data Book, 1993, which is hereby incorporated by reference. DAL1 controls RBS 130 functions, stores data from receiver 610 to memory 650, includes a real time clock to record time of data reception, and is used for selection of RS232 data transmission or modem data transmission.

DAL2 is a modem module manufactured by Dallas Semiconductor, part no. DS224524, and is described further in the Dallas Semiconductor Teleservicing Handbook, 1991, which is hereby incorporated by reference. It serves as an embedded modem for the RBS 130.

Another embodiment of the present invention uses power line carrier communications to provide the link between the receiver base stations 130 and the host computer 150. In some instances, cellular telephone modems may be utilized to provide the RBS 130/host computer 150 communications link.

The power supply 640 includes a battery backup system that will automatically switch in if power is lost. The battery backup will allow continuation of record tracking if power is lost. Battery backup also preserves memory so that record locations previously recorded are not lost. Under normal operation, the power supply 640 supplies a continuous trickle charge to the batteries.

Receiver Base Station Firmware

Figure 8:
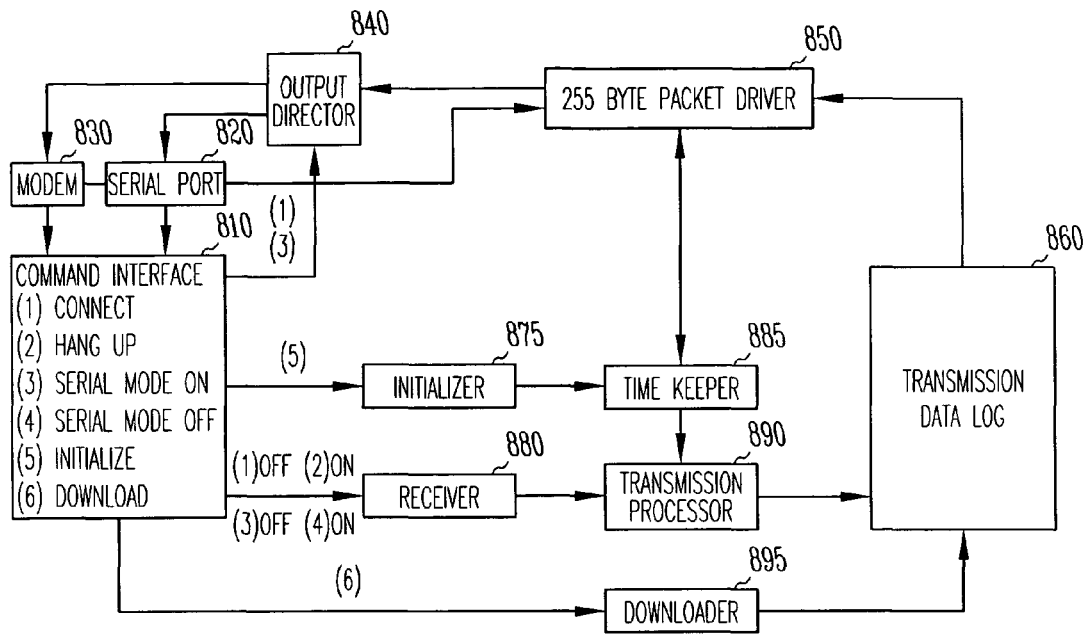
FIG. 8 is a flow diagram of a receiver base station firmware according to one embodiment of the present invention.

FIG. 8 is a flow diagram of a receiver base station firmware according to one embodiment of the present invention. The RBS 130 can communicate to the host computer 150 using either the serial port 820 or the modem 830. The command interface 810 controls the flow of data throughout the RBS 130. The serial port 820 uses a standard RS232 protocol running at 2400 Baud, 8 data bits, one stop bit, no parity. The modem 830 is Hayes compatible running at 2400 baud, 8 data bits, one stop bit, no parity. The output director 840 receives commands from the command interface 810 and selects I/O either through the serial port 820 or the modem 830 depending on which mode has been selected via the command interface 810.

Use of a modem 830 or serial port 820 does not limit the communications of the RBS 130 to the host computer 150.

These outputs may be connected to RF link hardware or optical link hardware in order to communicate with the host computer 150.

The command interface 810 interprets all commands from the host computer 150. A summary of these commands follows:

Connect

Informs the RBS 130 that it is being communicated with via the modem 830. Switches the output director 840 to modem operation. The radio frequency (RF) receiver 880 is turned off for the duration of the connection. Inhibiting the RF receiver 880 during communication with the host computer 150 prevents new data from being written to memory 650 while the present data is being downloaded.

Hang-up

Informs the RBS 130 that the host computer 150 has completed its exchange with the RBS 130 and that the RBS 130 can place the telephone line back on hook. The radio frequency receiver 880 is then turned on again.

Serial Mode On

Informs the RBS 130 that it is communicating with the host computer 150 via the serial port 820. Switches the output director to serial port 820 operation. The radio frequency receiver 880 is turned off during the duration of the connection.

Serial mode off

Informs the RBS 130 that the host computer 150 has completed its exchange with the RBS 130. The radio frequency receiver 880 is then reactivated.

Initialize

Instructs the RBS 130 to perform an initialization. This assigns a unique identification number to the RBS 130 and synchronizes its real time clock with the clock in the host computer 150.

Download

Figure 9:
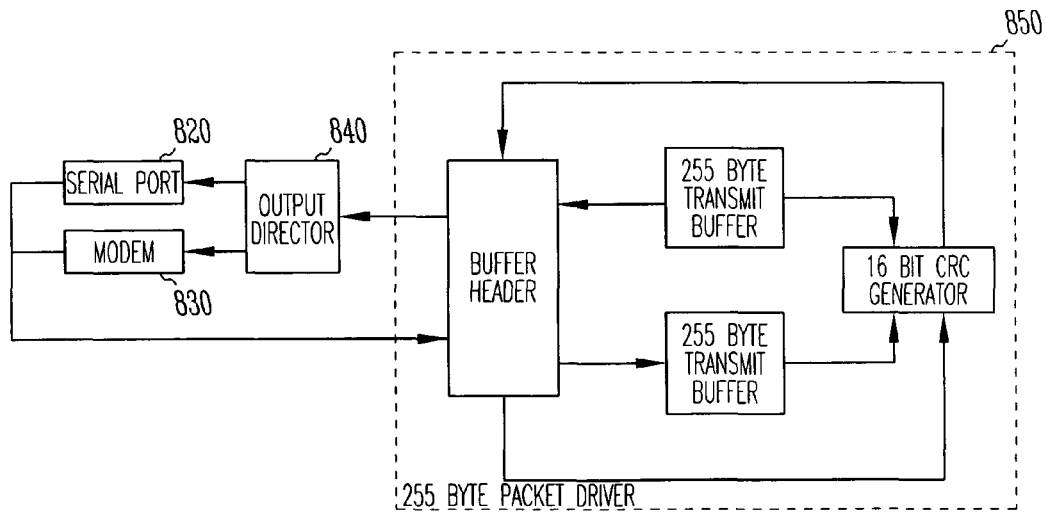
FIG. 9 is a flow diagram of a packet driver for serial and modem communications according to one embodiment of the present invention.
Figure 10:
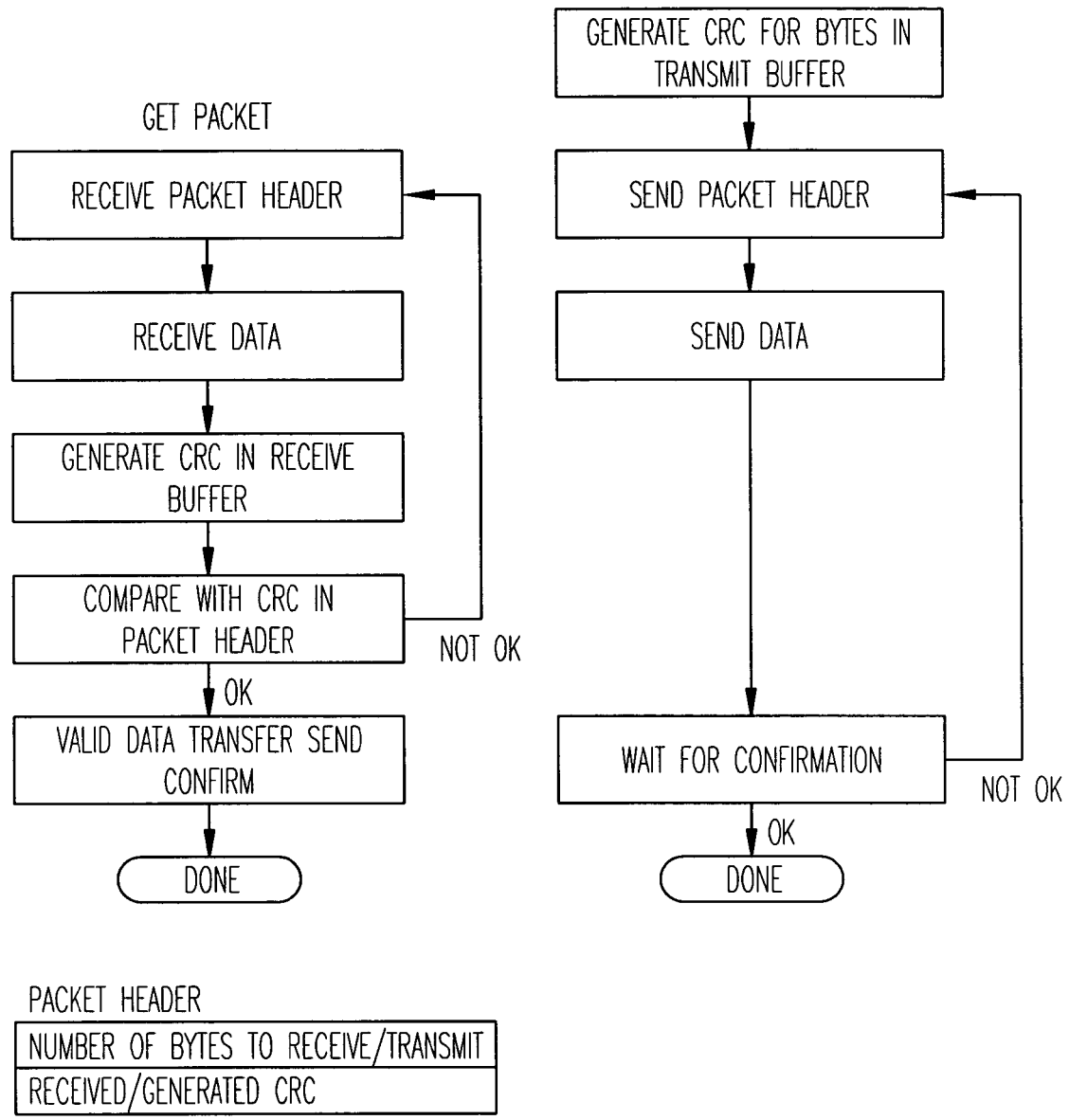
FIG. 10 is a flow diagram which shows the operation of the packet driver of FIG. 9.

Instructs the RBS 130 to transfer the contents of its transmission data log 860 to the host computer 150. Serial mode on or connect will have been invoked before this command can be executed. The details of this operation will be covered in a later section The 255 byte packet driver 850 used for both serial communications and modem communications is shown in FIG. 9. The operation of the packet driver 850 is demonstrated in FIG. 10. Packets of up to 255 bytes can be sent one at a time. These packets are preceded by a header which contains the total number of bytes in the packet. A 16 bit Cyclical Redundancy Check (CRC) is generated before the packet is sent and is also contained in the packet header. Once the packet is received a CRC is performed on the received data. This CRC is checked against the CRC contained in the packet header. If they do not match, the packet is re-sent until a valid data transfer (the CRC's are the same) is accomplished.

Figure 11:
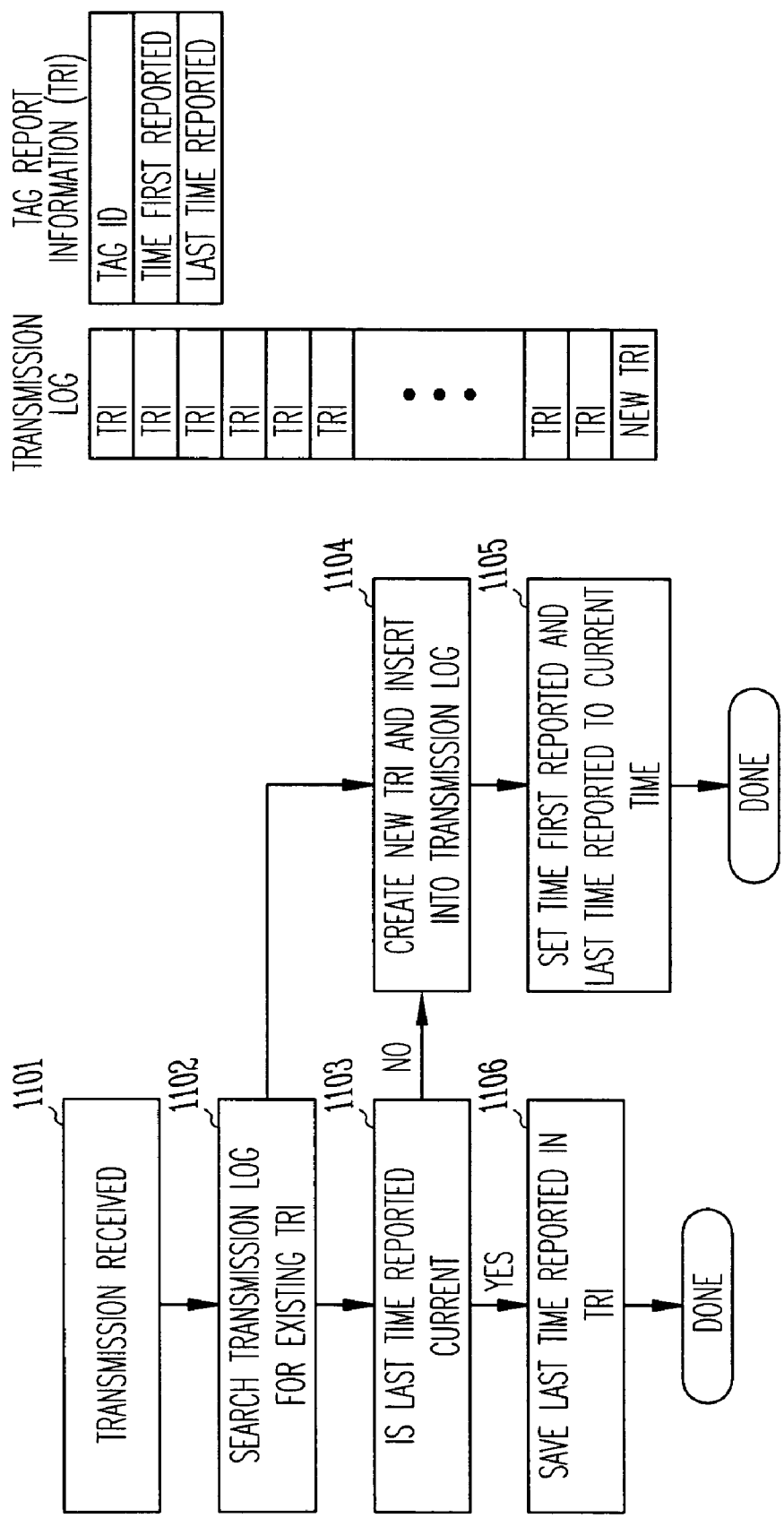
FIG. 11 is a flow diagram of a receive algorithm according to one embodiment of the present invention.

FIG. 11 demonstrates the chain of events following the reception of a valid radio transmission. In the event that a valid reception occurs, the RBS's microcontroller 620 will be provided an interrupt signal. The transmission data (tag ID number) will then be passed to the transmission processor. Once a valid reception has been established (step 1101) the transmission log is searched for a TRI (tag report information) (step 1102) which contains the ID of the received transmission. Once found it will determine if the TRI's last reported time was the previous transmission (the previous transmission is a transmission that was one frame backwards in time—see time windowing scheme, below). If a TRI is not found with a previous Last Time Reported (step 1103) or if one is not found at all, a new TRI will be created containing the current information (steps 1104, 1105). If the last time reported is current, then the last time reported is saved in the TRI (step 1106). The TRI's information can then be processed by the host computer 150 to determine when the tag 110 has entered and left or is still within the receiving range of the RBS 130. (see tracking algorithm, above).

Initializer

Figure 12:
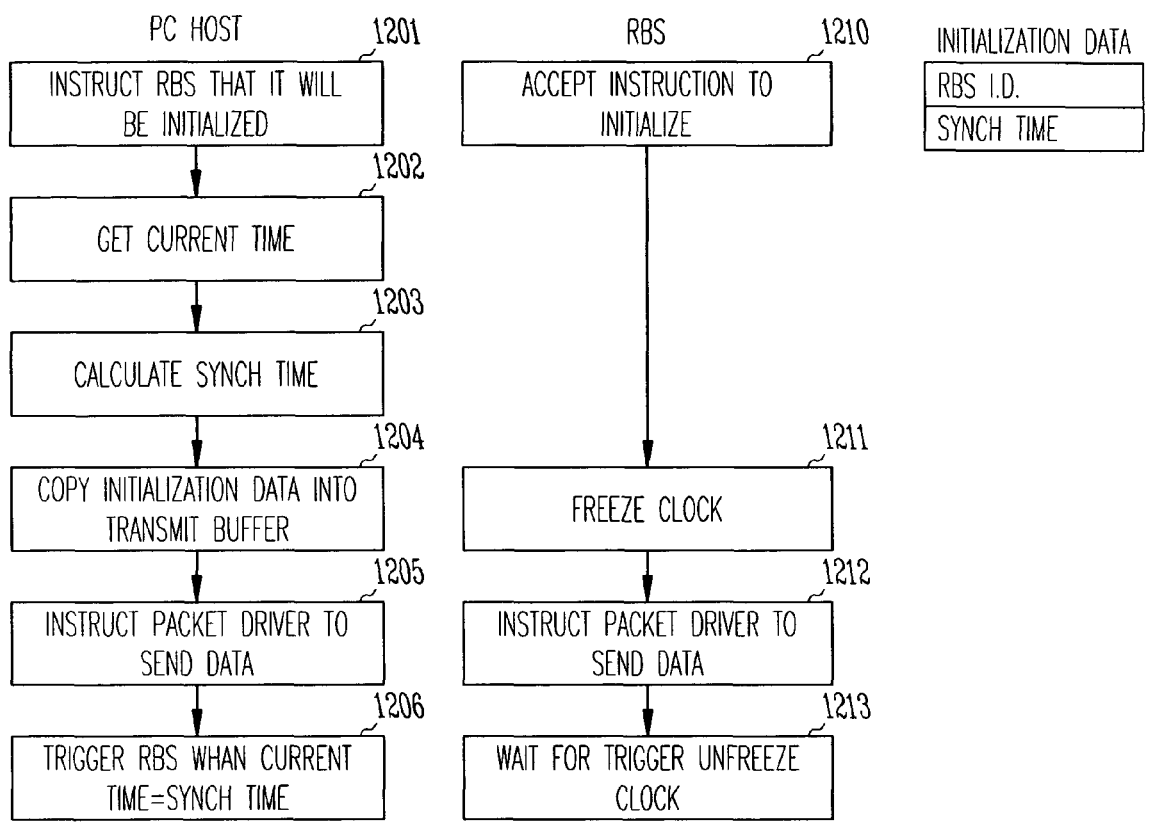
FIG. 12 is a flow diagram showing the initialization procedure of a receiver base station according to one embodiment of the present invention.

FIG. 12 illustrates the initialization procedure of the RBS 130. The information passed is the RBS ID and the synch time. The synch time is The host computer 150 sends an instruction to the RBS 130 to initialize the RBS (step 1201) which is then accepted by the RBS (step 1210). The host computer 150 gets the current time (1202), calculates the synch time (1203) and places the initialization information into the transmit buffer (1204). The synch time is determined by the host computer 150 by retrieving the current time and adding a positive offset to it. Once the RBS 130 has received the data (step 1205) the RTC (real time clock) and the RBS 130 RTC is frozen (1211), the RBS 130 acknowledges the data received (step 1212) and waits for a trigger from the host computer to unfreeze the clock (1213). The clock is then unfrozen after the initialization data is transferred and the synch time is equal to the current time (1206).

Downloader

Figure 13:
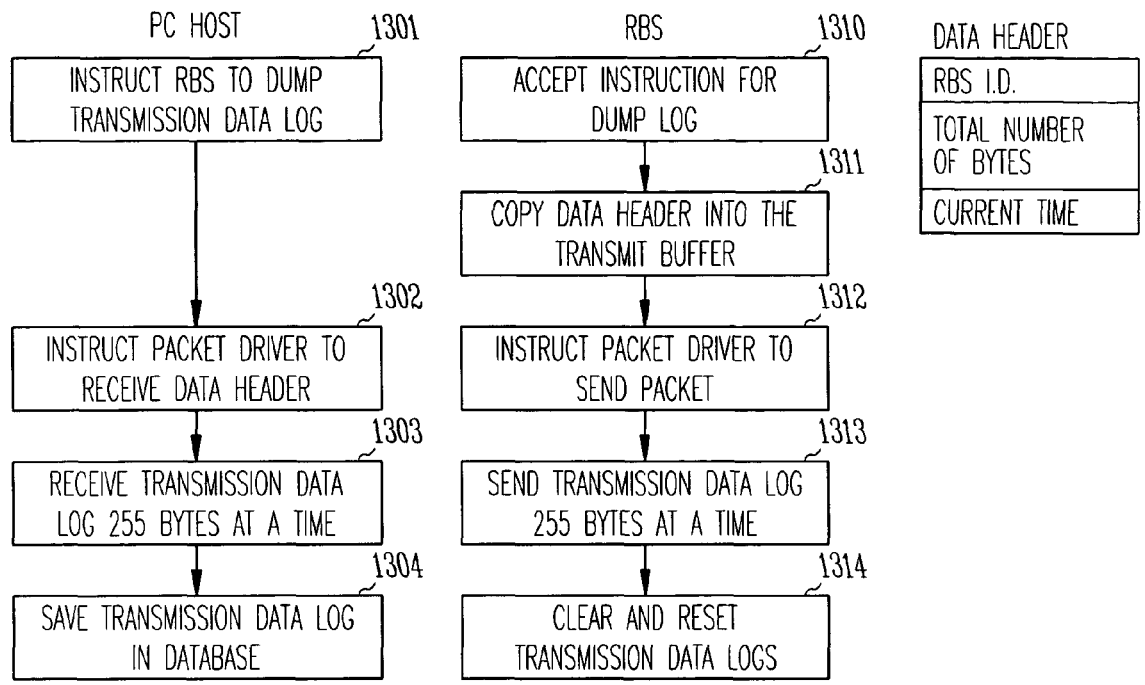
FIG. 13 is a flow diagram showing the download procedure from a receiver base station to a host computer according to one embodiment of the present invention.

FIG. 13 illustrates the downloading procedure according to one embodiment of the present invention. In this embodiment, the packet driver 850 is limited to 255 byte packets, so the transmission data log 860 is transferred in 255 block chunks. The host computer 130 instructs the RBS 130 to download the transmission data log 860 (step 1301). The RBS 130 accepts the instruction to download (1310), places the header in the transmit buffer (1311), and sends a packet (1312). The host computer 150 receives the data header 1302 and the RBS 130 sends data log at 255 bytes per transmission to the host computer 150 (steps 1313 and 1303). The RBS 130 clears and resets the transmission logs (1314) and the host computer 150 then saves the transmission data log (1304).

The first packet the downloader sends contains a data header. This header contains the RBS ID, the total number of bytes and the current time. This allows the host computer 150 to know how many bytes to expect and from which RBS 130 the data downloaded is retrieved.

Tag Operation

Figure 14:
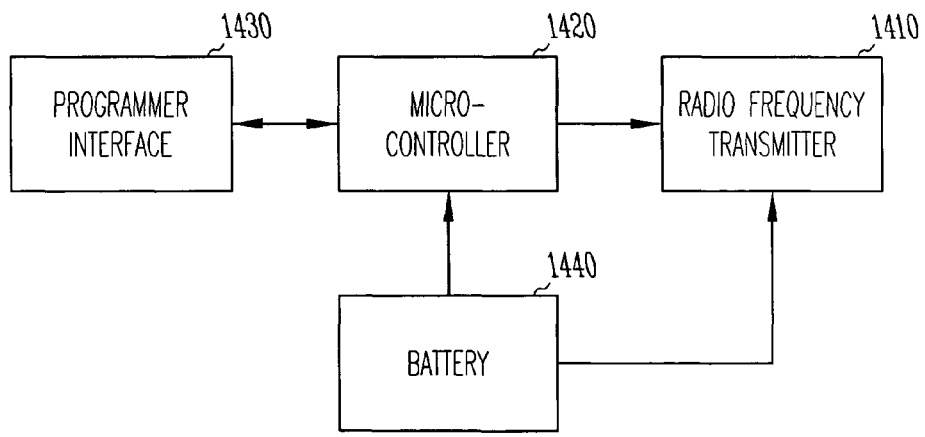
FIG. 14 is a block diagram of a tag according to one embodiment of the present invention.
Figure 15:
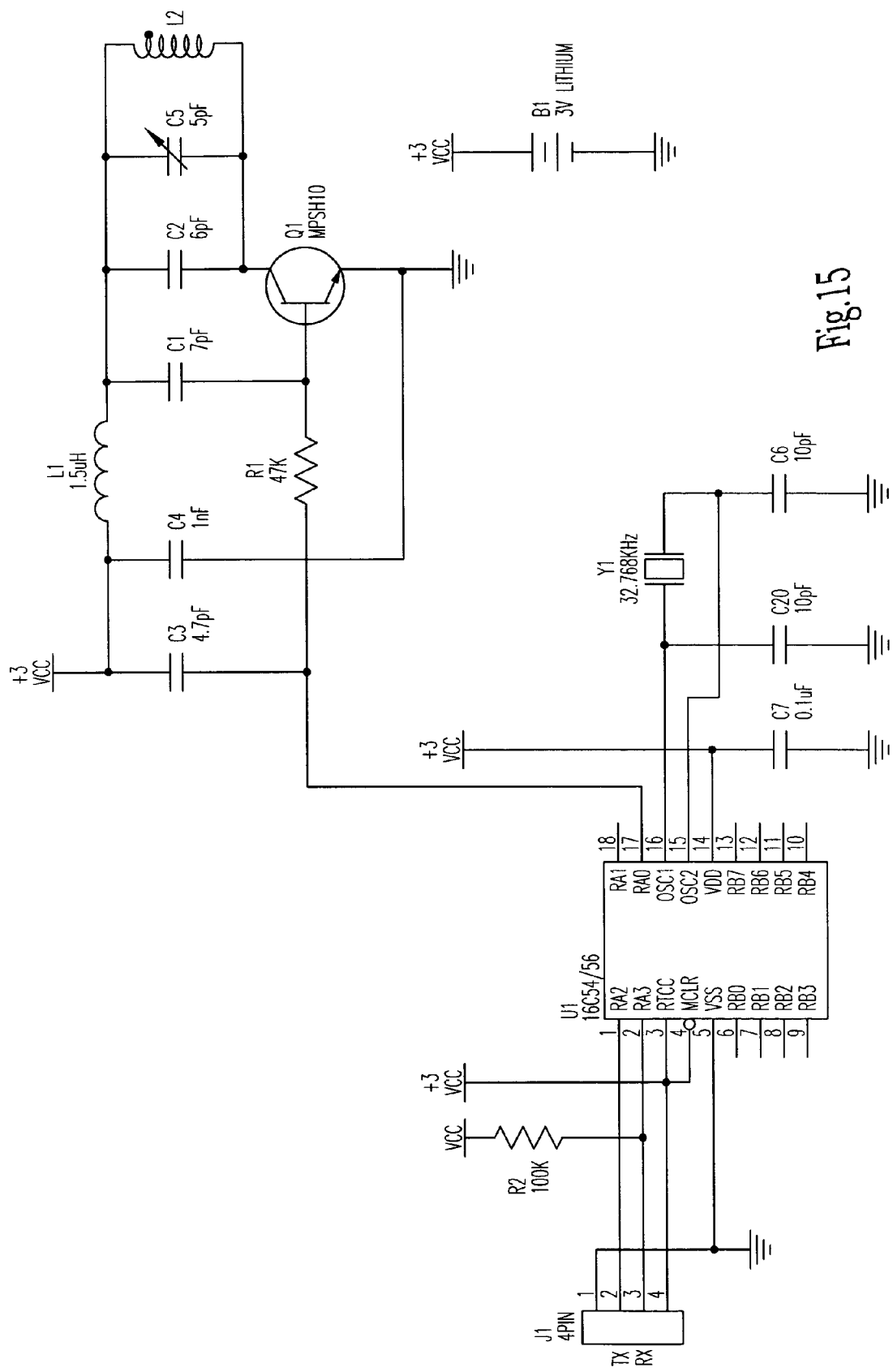
FIG. 15 is a schematic diagram of a tag according to one embodiment of the present invention.

A block diagram of the tag 110 according to one embodiment of the present invention is shown in FIG. 14. A schematic diagram of one embodiment of the tag 110 is shown in FIG. 15. The tag 110 comprises a radio frequency transmitter 1410 and microcontroller 1420 connected to a battery 1440. The microcontroller 1420 is connected to a programmer interface 1430 to program information to the tag 110 and to read information from the tag 110 for timing purposes.

In one embodiment the microcontroller 1420 is a Microchip Technology, Inc part no. PIC16C56LP/SO as described in the Microchip Databook, 1994, which is hereby incorporated by reference.

Jack J1 is used to connect to the programmer shown in FIG. 2. The RF transmitter 1410 comprises a 300 MHz oscillator modulated by output 17 of U1 in combination with transistor Q1.

Figure 16:
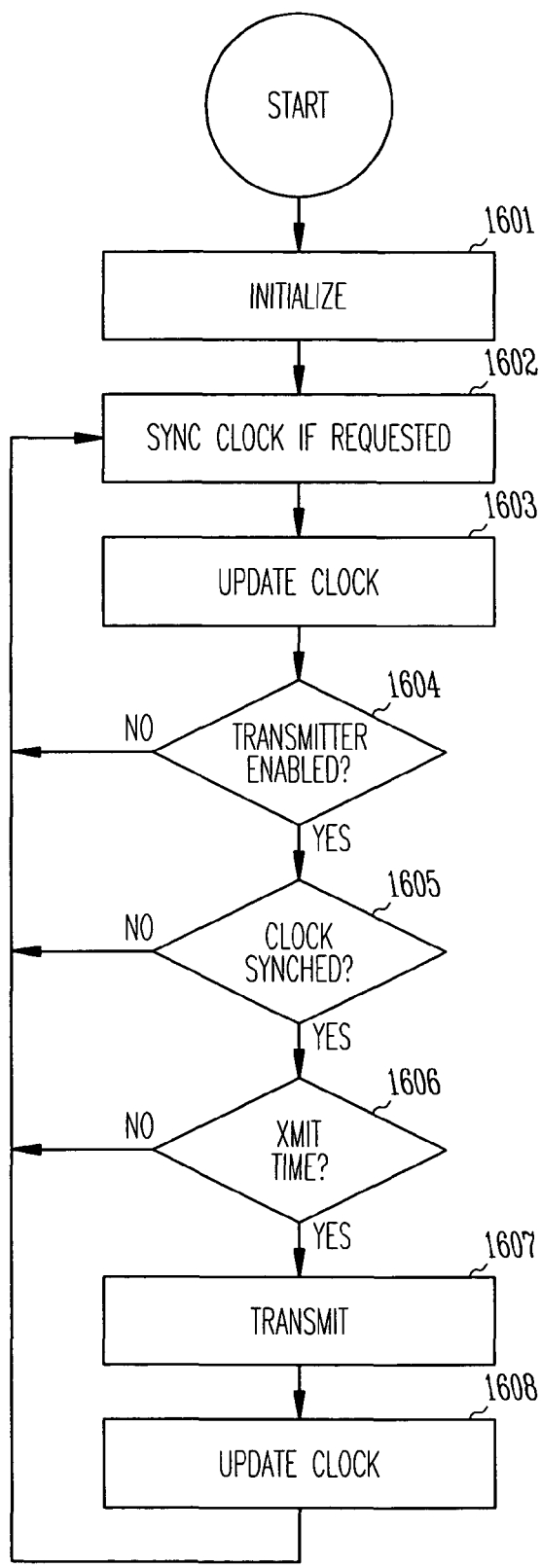
FIG. 16 is a flow diagram of a tag operation algorithm according to one embodiment of the present invention.

A flow diagram for the tag 110 microcontroller firmware is shown in FIG. 16. All tags 110 will transmit on the same carrier frequency (300 MHz in this embodiment). The tag 110 is initialized on powerup 1601 and if the tag 110 is connected to the tag programmer 155, then it will communicate with the host computer 150 to synchronize its local clock. A future time is downloaded to the tag 110 from the host computer 150 and the host computer 150 issues an instruction to synchronize the tag's 110 local clock to the host computer's 150 clock when the future time is reached (1602). The tag's 110 internal time clock registers are updated internally by the tag 110, and it is running independently of the host computer 150 (1603). A transmit enable bit is sent in step 1602 to instruct the tag 110 whether to enable or disable the transmitter 1410. This bit is read at step 1604 to enable the transmitter 1410 if the the tag 110 is being commissioned and disable the transmitter 1410 if the tag 110 is being decommissioned. If the transmitter 1410 is not enabled, the control will return to step 1602 until the transmitter 1410 is enabled.

Once the transmitter 1604 is enabled, a flag bit is checked to see if the clock was ever synchronized (1605). If not, control returns to 1602. If so, the tag 110 transmits when the tag's real time clock count equals the predetermined transmit time (steps 1606 and 1607). The clock is updated by the microcontroller 1420 (1608) before returning control to 1602.

In one embodiment, RF transmissions occur only on one frequency band, and contention can occur when two transmitters try to send at the same time. The time windowing scheme shown in FIG. 17 avoids contention by assigning a unique transmit time to each tag 110, which requires that the local clocks within the tags 110 must be synchronized. If the clock on a transmitter drifts, it may transmit during another tag's 110 time window. This can pose the threat of contention if both tags 110 are within the reception range of a particular RBS 130. To prevent contention time drift correction is incorporated into one embodiment of the present invention. One can calculate the drift rate of each tag 110 clock by monitoring the times of each successive transmission. With this information, a correction factor is used to follow the identity of each tag 110 clock through nominal drifts. Long term, the tag 110 will be recalibrated when it is associated with a new record (e.g., when the tag is decommissioned or when the tag is commissioned) or when the battery is replaced.

In one embodiment a tag 110 transmits only during its time window of length Δt (FIG. 17). If N tags are implemented then the time it will take for all the tags to finish reporting is T=Δt*N. After this time the cycle can start again and a tag 110 reports every T seconds. A DOS based computer will be used to set the local clocks on each of the tags. In one embodiment a very accurate clock is used to set the times of all of the clocks. It is possible to synchronize the clock of the host computer 150 according to the National Bureau of Standards WWV atomic timebase using readily available commercial software dedicated to updating the system clock of host computer 150. For example, Precision Time (a trademark of Crystalogic of Nashville, Tenn.) may be used to synchronize the host computer 150 clock. If these clocks are set to plus or minus one second and variation in the Tag's local clock of ¼ second is allowed, the minimum Δt is 2.25 seconds. For a system of 500 tags, the time required for all tags to report will be 18.75 minutes.

$T=N*\Delta t$ $T=500*2.25 \text{ sec}$ $T=1{,}125 \text{ sec}=18.75 \text{ min}$ The tags transmit a 16 bit ID code in two 8 bit bytes. In addition to the code, an error detection byte is transmitted with each ID byte. The error detection byte is used by the RBS 130 receiver module to discern valid transmissions. The data is transmitted in the format shown in FIG. 18. Each byte begins with a start bit and ends with a stop bit, both of which the RBS 130 receiver module will use for synchronization. Ones and zeros will take the same amount of time to transmit. However, ones will transmit high for ⅔ of one period while zeros will transmit high for ⅓ of a period. One period is equal to three periods of the transmit timing clock shown in FIG. 18. In this embodiment the data transmission rate is 910 bps. Each data byte will be separated from its error detection byte by 5.5 milliseconds and each set of data bytes and error detect bytes will be separated by 12 milliseconds.

Figure 19:
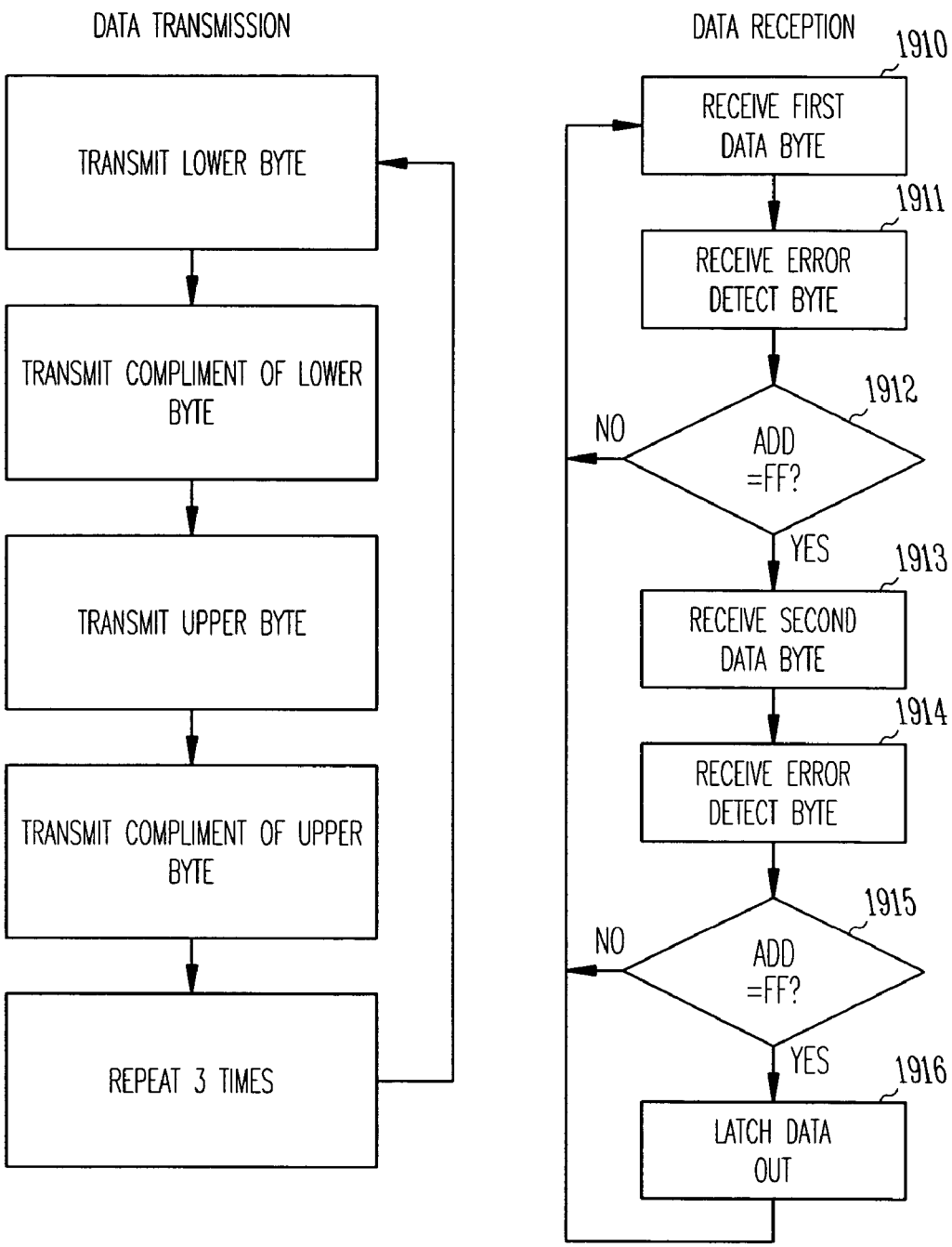
FIG. 19 is a flow diagram showing the data transmission and reception according to one embodiment of the present invention.

Data transmission and reception flow is shown in FIG. 19. When the tag 110 has reached its transmit time interval, it transmits its ID code and error detection bytes three times in succession (steps 1902).

The RBS 130 receiver module will continually poll its input for the presence of a data transmission (step 1910). Once the RBS 130 receiver module has detected an incoming byte, it will save the byte, receive an error detect byte (1911), add it to its error detect byte and determine if the transmission was valid (1912). In one embodiment the error detection byte is the complement of the incoming byte for error detection purposes. If the addition of the incoming byte and its associated error detect byte is FFh, then the byte is valid. If a valid transmission was received the next byte will be examined and checked against its error detection byte (steps 1913, 1914, and 1915). If the two consecutive ID bytes test valid, the ID will be latched out for the RBS 130 processor to time stamp and save (1916).

Tag Time Synchronization

Theory and Operation

Definitions:

Δt (delta t): The time between transmissions of two tags with adjacent ID's.

Frame: Unit of time in which all tags transmit once before transmitting again.

Frame Size: The amount of time it takes for all tags to report and the interval time between to transmissions from the same tag.

Current time relative to zero: The frame is referenced at the tag with ID zero.

Tag Counter: Counter within tag. Acts as tags transmit interval clock

Theory

In one embodiment of the present invention, each tag 110 transmits at a predefined interval as dictated by its ID number. The ID number is assigned by the host computer 150 and downloaded to the tag 110 during programming. The time between two concurrent transmissions of the same tag 110 is defined as the frame size. The frame size is dictated by the minimum amount of time that it takes for all the tags to transmit and the amount of time that must be allowed between tag 110 transmissions to allow for drift in the tag's local clocks. The first frame always starts at 00:00 hours and the number of frames must be divisible into a 24 hour day. Therefore it may be necessary to adjust the frame size so that there are an integer number of frames per day. The calculations are as follows.

| given | n: | number of tags |
|---|---|---|
| | ID: | ID of tag to be programmed |
| | Δt: | minimum interval between transmissions of two tags with adjacent ID's. |

Frame Size=n*_Δt

Frames per Day=⌊24 hours/Frame Size⌋

Adjusted Frame Size=24 hours/Frames per Day

Adjusted Δt=⌊Adjusted Frame Size/n⌋

This adjusts frame size so that the first frame starts at 00:00 hours and the last frame ends at 24:00 hours.

Now that Δt and Frame Size have been properly chosen the tag clocks must be synchronized. Each tag 110 has a real time clock. These clocks are not 24 hour clocks but rather frame size clocks. The clocks start at zero and are incremented such that once a clock reaches frame size it transmits. These counters are synchronized with the computer so that the end of the count will fall at exactly the transmit time identified by the tag's ID. Tag 0 is synchronized so that its first frame begins at 00.00 hours and all other clocks are synchronized by their transmit time relative to tag 0. The synchronization is accomplished as follows.

ID Transmit time relative to zero (IDtrz)=ID*Δt

Current time relative to zero(CRZ)=current time % frame_size (where % denotes modulus or remainder)

if (IDtrz>CRZ) then count=Frame size–(IDtrz–CRZ) else count=IDtrz–CRZ

Where count is the time the tag's local clock will be set to.

Time Drift Correction

The real time clock counter is driven by a crystal oscillator. While crystal oscillators have a high degree of accuracy, there will still be some variation in their frequency from their specified nominal frequency. The consequence of this inaccuracy is that the tag's 110 local clocks will have some degree of drift which may pose the problem of tags 110 transmitting outside their predetermined window. If this were allowed to happen, two tags 110 may transmit at the same time and their signals could contend. Due to this inherent drift, the real time clock must be adjusted periodically to maintain its accuracy. This correction is performed by keeping statistical records on the individual tags 110 and adjusting the clock counter as necessary. The host computer 150 can determine when and by how much the tag 110 should make an adjustment to its clock counter. Each time the tag 110 is programmed, the host computer 150 will examine the tag's real time clock and determine the amount of drift it has experienced since the last time it was programmed. In addition to its current time, the tag 110 will report any correction factors it has been using to maintain its real time clock. The host computer 150 will use this information to calculate a new correction factor and this factor will be downloaded to the tag 110. An adjustment counter is implemented in the tag 110 so that, at predetermined intervals, a count will be either added to or subtracted from the real time clock counter. The algorithm to determine the correction factors is as follows:

| Definitions: | |
|---|---|
| Time correction count: | Value that the adjust counter will count up to before it makes an adjustment |
| Adjust value: | Value that will be added to or subtracted from the real time clock counter |
| Out_count | Real time count since last synchronization. |
| Count | Count in current frame relative to ID of tag |
| PC count | Expected value of count when tag is initialized |
| Offset = PC count − count | |
| Adjust value = sign(offset) * 1 | the sign is the direction of the offset (positive or negative) |
| adjust value = abs(out_count/offset); | where abs is the absolute value so that the answer is always positive |
| adjust counter | a counter within the tag 110 that signals a tag time drift correction when the counter equals the time correction count |
| TAG: | when (adjust counter = time correction count) update count by adjust value. |

Operation

Figure 20:
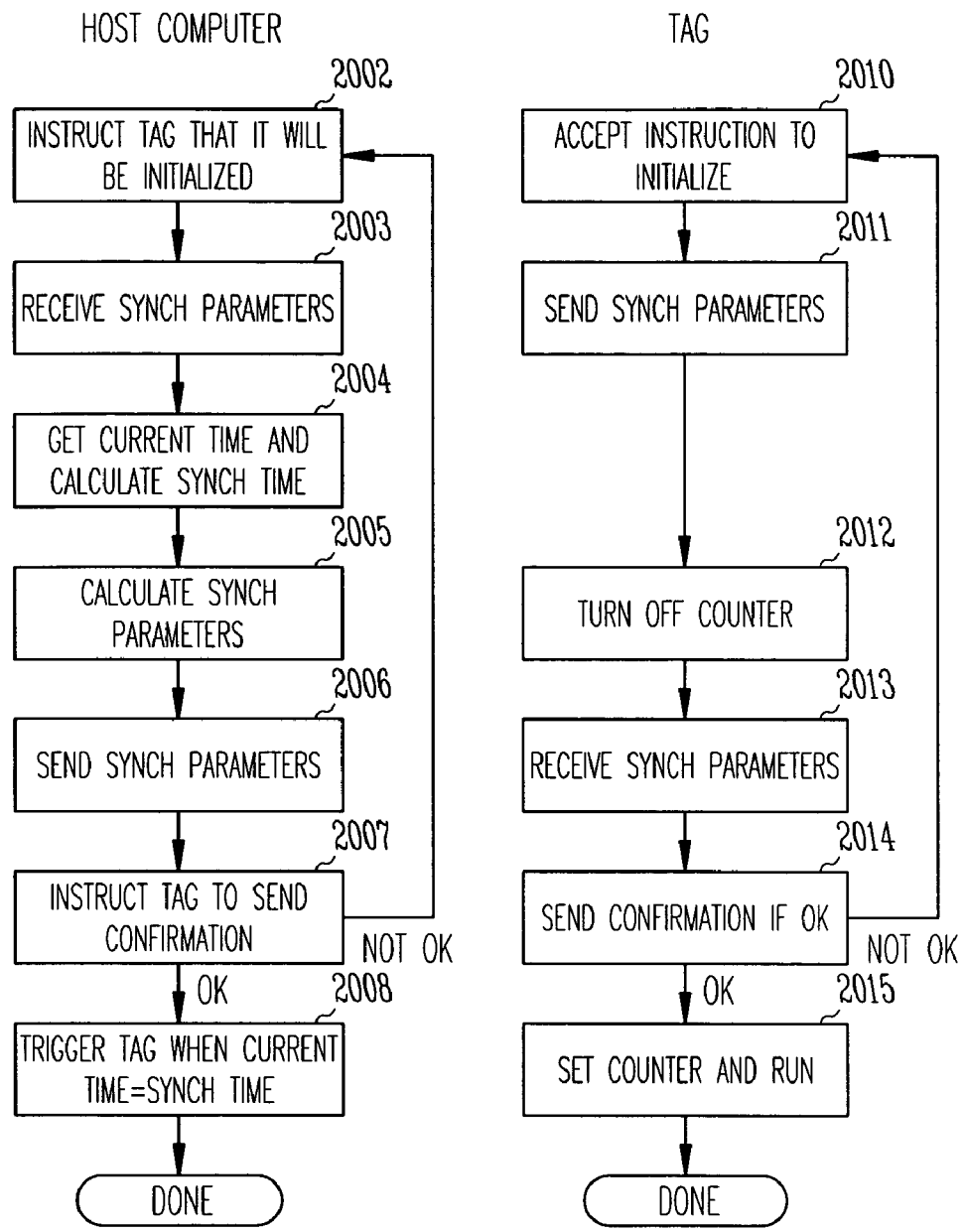
FIG. 20 is a flow diagram illustrating the synchronization scheme of the tag and host computer according to one embodiment of the present invention.

FIG. 20 shows the synchronization scheme of the tag 110. In one embodiment, communications are accomplished via serial port at 300 baud, 8 bits, no parity, 1 stop bit.

The tag is placed in tag programmer 155 and the host computer 150 instructs tag 110 that it will be initialized (step 2002) and the tag 110 accepts the instruction (2010). The tag 110 transmits the synch parameters (2011) and host computer 150 receives the synch parameters from the tag 110 (2003). The tag's 110 local counter is deactivated (2012). The host computer 150 uses the synch parameters as a measure of the tag's 110 current time and calculates an appropriate offset to compensate for drift. The host computer then adds an offset to the current time and sends the synch parameters to the tag 110 (2006), which are received by the tag 110 (2013). The tag is instructed to send a confirmation (2007) which is transmitted by the tag 110 (2014). The host computer 150 then transmits a trigger signal (2008) which triggers the tag counters (2015) at the predetermined time (set by the host computer 150).

Record Locator or Sniffer

One embodiment of the present invention includes a record locator to assist the subject searching for a record once they have established its general location. One embodiment of the record locator is a handheld distance sensing receiver (akin to an RBS 130) which detects signal strength for a particular tag identification code which is preprogrammed into the device. This device would indicate to a user if she is approaching the record. However, this presumes that the transmit time of the tag 110 is sufficiently rapid to reasonably sense.

Another embodiment of a record locator requires radio receivers with audio indicators attached to each tag 110 and a hand held, programmable transmitter to activate the audio indicator on a particular record. The transmitter is programmed with the unique identification code of the particular record being searched for. The transmitter continually transmits this identification code and, when the transmitter has entered the receiving range of the device attached to the record, the audio indicator is activated. This allows the subject involved in the search to locate a single record intermixed among a number of other records or a record that has been placed in a inconspicuous location.

The multipurpose tracking system described is useful for generating a proprietary dynamic data base in the memory of the host computer 150 which represents a complete record of all past and present locations of the circulating records. At convenient intervals of time all of the dynamic current data base is transferred to an archive sector of the host computer 150 memory. When placed in this storage format, the data base can be searched and manipulated in the same way as the current dynamic data record. This feature of the invention makes it possible to extract a very wide range of features including but not limited to:

1. Given a specific record ID, what is the current or most recent receiver range or ranges to which it has reported. Overlapping receiver ranges allow increased location resolution.
2. List all records with their locations which have been in circulation for more than some specified duration.
3. Compile statistical characterization of load on services or equipment.

This disclosure has discussed the use of some embodiments of the present invention for record tracking, however, as stated earlier, several other applications may be performed using the present invention, and the example of record tracking was not intended to be exclusive or limiting. The present invention can also be used for tracking equipment, personnel, and any other movable object. In addition, the particular data collection apparatus and methods disclosed herein may be modified without departing from the scope and spirit of the present invention.

Although specific embodiments have been illustrated and described herein, it will be appreciated by those of ordinary skill in the art that any arrangement which is calculated to achieve the same purpose may be substituted for the specific embodiment shown. This application is intended to cover any adaptations or variations of the specific invention. Therefore, it is manifestly intended that this invention be limited only by the claims and equivalents thereof.

We claim:

1. A method for controlling a reception region, comprising:
   setting up a receiver base station including an antenna;
   attaching a plurality of transmitters to a plurality of objects, each object of the plurality of objects having a transmitter of the plurality of transmitters, each transmitter adapted to transmit a unique identifier;
   adjusting sensitivity of the receiver base station by controllably attenuating signals received by the antenna;
   if the reception range is less than a desired reception range, decreasing attenuation; and
   if the reception range exceeds the desired reception range, increasing attenuation.

2. The method of claim 1, wherein the desired reception range is a function of room size.

3. The method of claim 1, wherein the reception range is isotropic.

4. The method of claim 1, wherein the reception range is anisotropic.

5. The method of claim 1, wherein the reception range is adjustable to a few feet.

6. The method of claim 1, wherein the receiver base station communicates to a host computer by a system including modulations over AC power lines.

7. The method of claim 1, wherein the receiver base station communicates to a host computer by a system including radio communications.

8. The method of claim 1, wherein the receiver base station communicates to a host computer by a system including a dedicated hardwired link.

9. The method of claim 1, wherein the receiver base station communicates to a host computer by a system including a computer network link.

10. A method for controlling overlap in reception regions, comprising:
    setting up a plurality of receiver base stations, each receiver base station having an antenna with a reception pattern which defines a reception region;
    attaching a plurality of transmitters to a plurality of objects, each object of the plurality of objects having a transmitter of the plurality of transmitters, each transmitter adapted to transmit a unique identifier;
    for each receiver of the plurality of receivers, adjusting sensitivity of the receiver by attenuating signals received by the antenna, wherein the reception regions for the plurality of receivers are adjusted to overlap.

11. The method of claim 10, wherein the reception region of at least one receiver base station of the plurality of receiver base stations is a function of room size.

12. The method of claim 10, wherein the reception region of at least one receiver base station of the plurality of receiver base stations is isotropic.

13. The method of claim 10, wherein the reception region of at least one receiver base station of the plurality of receiver base stations is anisotropic.

14. The method of claim 10, wherein the reception region of at least one receiver base station of the plurality of receiver base stations is adjustable to a few feet.

15. The method of claim 10, wherein at least one receiver base station of the plurality of receiver base stations communicates to a host computer by a system including modulations over AC power lines.

16. The method of claim 10, wherein at least one receiver base station of the plurality of receiver base stations communicates to a host computer by a system including radio communications.

17. The method of claim 10, wherein at least one receiver base station of the plurality of receiver base stations communicates to a host computer by a system including a dedicated hardwired link.

18. The method of claim 10, wherein at least one receiver base station of the plurality of receiver base stations communicates to a host computer by a system including a computer.

19. In a radio frequency tracking system comprising a plurality of transmitters and a plurality of receivers, each receiver of the plurality of receivers having an antenna with a reception pattern which defines a reception region, an apparatus for controlling reception regions, comprising an attenuator, inserted between a receiver of the plurality of receivers and its associated antenna for adjusting the reception region which the antenna receives, wherein the reception region of each of the plurality of receivers is adjustable for controlling overlap of reception regions, each transmitter of the plurality of transmitters is adapted to transmit a unique identifier, and each receiver of the plurality of receivers is adapted to receive the unique identifier from a transmitter in its reception region to identify location of the transmitter in its reception region.

20. The apparatus of claim 19, wherein the reception region of at least one receiver of the plurality of receivers is a function of room size.

21. The apparatus of claim 19, the reception region of at least one receiver of the plurality of receivers is isotropic.

22. The apparatus of claim 19, wherein the reception region of at least one receiver of the plurality of receivers is anisotropic.

23. The apparatus of claim 19, wherein the reception region of at least one receiver of the plurality of receivers is adjustable to a few feet.

24. The apparatus of claim 19, wherein at least one receiver of the plurality of receivers is adapted to commu nicate to a host computer by a system including modulations over AC power lines.

25. The apparatus of claim 19, wherein at least one receiver of the plurality of receivers is adapted to communicate to a host computer by a system including radio communications.

26. The apparatus of claim 19, wherein at least one receiver of the plurality of receivers is adapted to communicate to a host computer by a system including a dedicated hardwired link.

27. The apparatus of claim 19, wherein at least one receiver of the plurality of receivers is adapted to communicate to a host computer by a system including a computer network link.

* * * * *

UNITED STATES PATENT AND TRADEMARK OFFICE
CERTIFICATE OF CORRECTION

PATENT NO. : 7,019,642 B2  Page 1 of 1
APPLICATION NO. : 10/648036
DATED : March 28, 2006
INVENTOR(S) : Nelson et al.

It is certified that error appears in the above-identified patent and that said Letters Patent is hereby corrected as shown below:

In column 18, line 55, in Claim 18, after "computer" delete "." and insert -- network link. --, therefor.

In column 19, line 7, in Claim 21, after "claim 19," insert -- wherein --.

Signed and Sealed this

Eighth Day of August, 2006

JON W. DUDAS
*Director of the United States Patent and Trademark Office*